(12) United States Patent
Vidal et al.

(10) Patent No.: US 10,390,407 B2
(45) Date of Patent: Aug. 20, 2019

(54) THERAPEUTIC ILLUMINATION SYSTEM

(71) Applicant: SVLux Corporation, Boise, ID (US)

(72) Inventors: Linus Vidal, Boise, ID (US); Darrell Adams, Portland, OR (US)

( * ) Notice: Subject to any disclaimer, the term of this patent is extended or adjusted under 35 U.S.C. 154(b) by 0 days.

(21) Appl. No.: 15/912,699

(22) Filed: Mar. 6, 2018

(65) Prior Publication Data

US 2018/0199411 A1 Jul. 12, 2018

Related U.S. Application Data

(63) Continuation of application No. 14/983,578, filed on Dec. 30, 2015, now Pat. No. 9,913,345.

(60) Provisional application No. 62/098,927, filed on Dec. 31, 2014.

(51) Int. Cl.
| | | |
|---|---|---|
| H05B 33/08 | (2006.01) |
| H05B 37/02 | (2006.01) |
| F21V 29/61 | (2015.01) |
| F21V 29/67 | (2015.01) |
| F21V 29/74 | (2015.01) |
| A01G 7/04 | (2006.01) |
| A01G 9/20 | (2006.01) |
| A61N 5/06 | (2006.01) |
| F21Y 115/10 | (2016.01) |

(52) U.S. Cl.
CPC ......... *H05B 33/0872* (2013.01); *A01G 7/045* (2013.01); *A01G 9/20* (2013.01); *A61N 5/0616* (2013.01); *F21V 29/61* (2015.01); *F21V 29/67* (2015.01); *F21V 29/74* (2015.01); *H05B 33/0803* (2013.01); *H05B 33/083* (2013.01); *H05B 33/0812* (2013.01); *H05B 33/0818* (2013.01); *H05B 33/0851* (2013.01); *H05B 33/0854* (2013.01); *H05B 37/0227* (2013.01); *H05B 37/0254* (2013.01); *A61N 2005/0651* (2013.01); *F21Y 2115/10* (2016.08); *Y02B 20/383* (2013.01)

(58) Field of Classification Search
CPC ............ H05B 33/0812; H05B 33/0818; H05B 33/083; H05B 33/0851; H05B 33/0854; H05B 33/0872
USPC ................ 315/192, 250, 291, 294, 307, 312
See application file for complete search history.

(56) References Cited

U.S. PATENT DOCUMENTS

| | | | | |
|---|---|---|---|---|
| 2009/0323321 A1* | 12/2009 | Paolini | ................ | H05B 33/086 362/231 |
| 2010/0264833 A1* | 10/2010 | Van Endert | ............ | H03K 17/94 315/152 |
| 2012/0326612 A1* | 12/2012 | Kirsten | ................ | G09F 19/205 315/153 |
| 2015/0035437 A1* | 2/2015 | Panopoulos | ............ | F21V 14/02 315/112 |
| 2015/0054422 A1* | 2/2015 | Koo | .................... | H05B 33/0872 315/250 |

(Continued)

*Primary Examiner* — Tung X Le
(74) *Attorney, Agent, or Firm* — Brian J. Pangrle

(57) ABSTRACT

A therapy system includes a controller; LEDs; LED supply circuitry operatively coupled to the LEDs, where the controller is operatively coupled to the LED supply circuitry for control of the LED supply circuitry; and a sensor that senses information of an object, where the sensor is operatively coupled to the controller and where the controller controls the LED supply circuitry based at least in part on the information to therapeutically illuminate the object via one or more of the LEDs.

18 Claims, 25 Drawing Sheets

(56) References Cited

U.S. PATENT DOCUMENTS

2015/0374452 A1\* 12/2015 Saito ................ A61B 90/36
600/424

\* cited by examiner

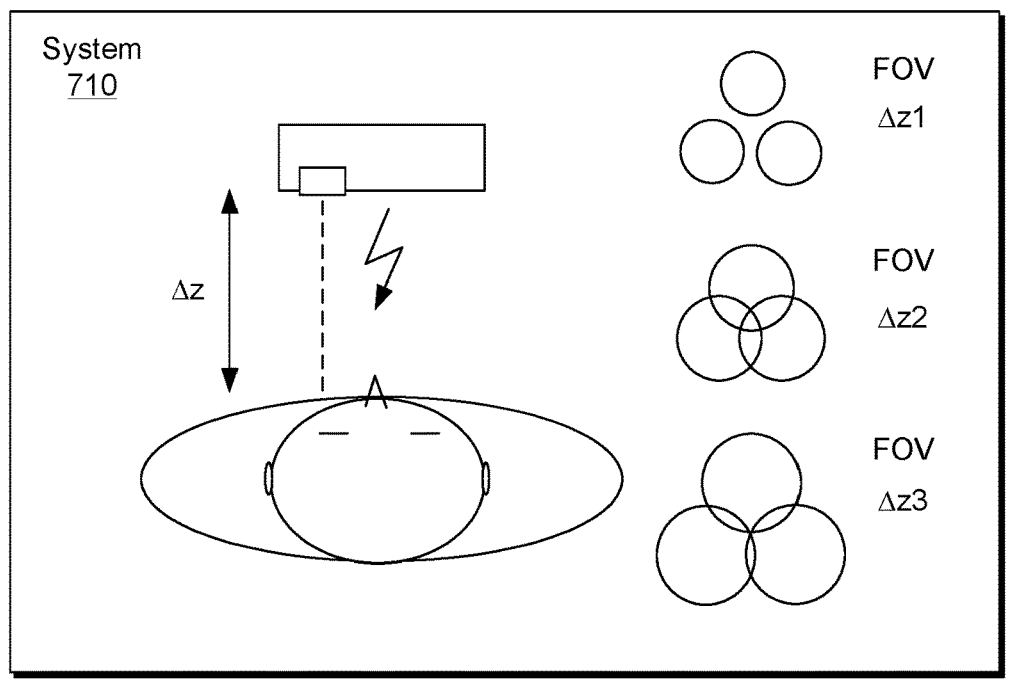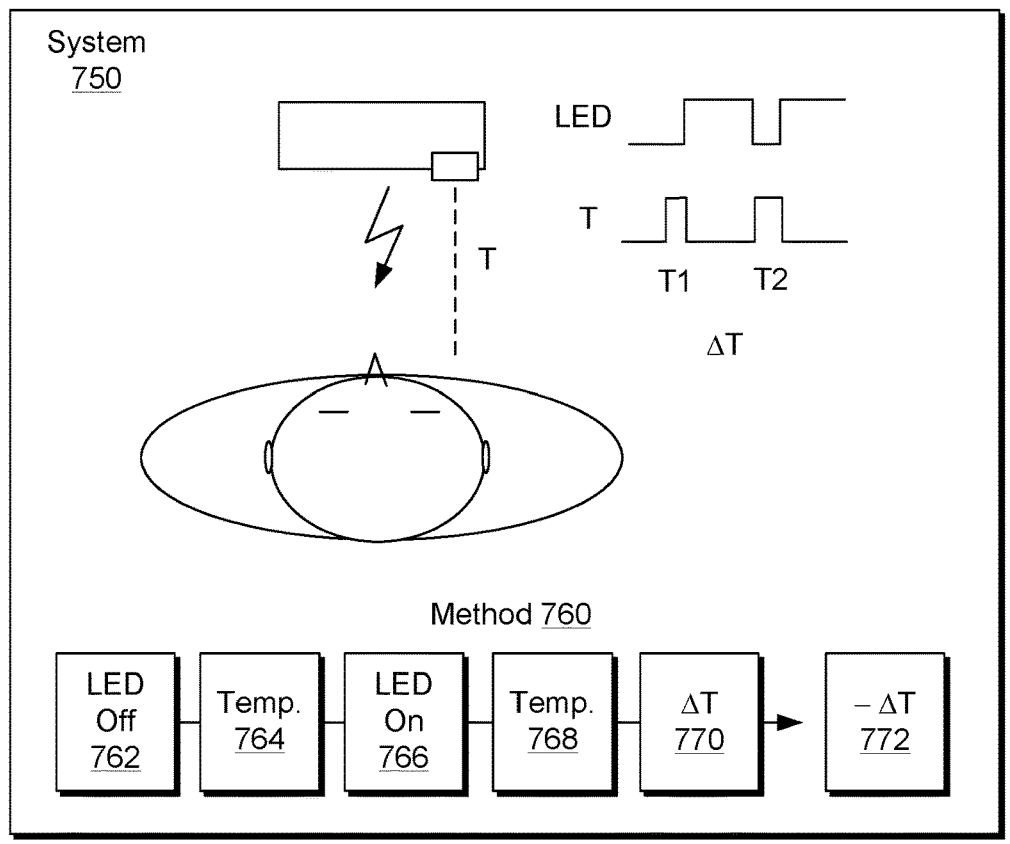
Fig. 7

Table 900

| Driver | Board | Description |
|---|---|---|
| I/O | UI-Board/IO-BOARD | Access to buttons on UI-Board, access to status LEDs on Boards. |
| WIFI | UI-Board | Access to the WIFI module |
| Buttons | UI-Board | Encoder Button and Buttons |
| I2c | IO-Board | Access to LED Current Controller |
| RS-485 | UI-Board IO-Board | Multi-point Board to Board Communication |
| ETHERNET | UI-Board | Access to the ETHERNET Controller |
| Analog | IO-Board | Access to Analog Inputs for temperature control |
| SPI | UI-Board | Access to the SPI interface |
| SD | UI-Board | Access to the SD-Card (SPI) |
| Quad-Encoder | UI-Board | Access to the quadrature encoder (rotary button) |

Fig. 9

Table 1000

| Utility | Board | Description |
|---|---|---|
| InterBoard Com | UI-Board<br>IO-BOARD | Transport layer for inter-board communication. |
| UI | UI-Board | Access to the UI and access to LCD, QUAD-ENC and I/O drivers (e.g., including buzzer/audio). |
| JSON-Store | UI-Board | Unified access to JSON-Store |

Fig. 10

Storage 1100

" Configuration
" LED
" Fan
" Timeouts
" Temperature
" Firmware Version
" Users
" Warning Level
" Error Level
" User Interface
" ETHERNET Interface
" WIFI wireless
" Networking
" Machine Controls
" Machine Status
" Logging
" Other

Fig. 11

Services 1200

1210 Bootstrap Service
    Loads, validates an re-programs device with the encrypted/signed firmware (e.g., from the SD card).
    Restores to previous version.
    Runs the firmware.

1220 Condition Service:
    Checks machine is running within specified boundary parameters.
    Temperature range, time, logs error conditions, etc.
    Monitors and logs into the store temperature, fan-speeds, etc.
    Detects issues and provides alerts for preventative maintenance in case of issue(s) like fan running too fast in comparison to other fans, LED overheating, etc.

1230 Thermal Management Services:
    Ensures set dosage (e.g., intensity and time) is delivered within appropriate boundaries of system.
    Increases, decreases LED Intensity and Fan Speed to meet desired requirements (e.g., based on PID-Fuzzy logic model).
    Store access for operation.
    Updates Store with Machine Status.

1240 User Service:
    Parses commands from the various interfaces, updates the Store
    Commands as controls or queries.

Fig. 12

| Protein | Host plant | Company/ Organization | Indication/ application | Development stage |
|---|---|---|---|---|
| Animal vaccine | tobacco cells | USA, Dow AgroSciences | Newcastle disease in chicken | approved by USDA 2/2006 |
| Enzyme, Glucocerebrosidase | carrot cells | Israel, Protalix Biotherapeutics | Gaucher disease | phase 3 |
| Monoclonal antibody | tobacco | USA, Planet Biotechnology, | prophylaxis of caries | phase 2 |
| Enzyme, gastric lipase | maize | France, Meristem Therapeutics | Cystic Fibrosis | phase 2 |
| Antibody, cancer vaccine | tobacco | USA, Large Scale Biology | non-Hodgkin Lymphoma | phase 2 |
| Alpha-Interferon | duckweed | USA, Biolex | hepatitis C | phase 2 |
| Antigene | potato | USA, Arizona State University | hepatitis B | phase 2 |
| Human intrinsic factor | *Arabidopsis* | Denmark, Cobento Biotech | vitamin B12 deficiency | phase 2 |
| Antibody | tobacco | USA, Planet Biotechnology | cold caused by Rhinoviruses | phase 2 |
| Insulin | safflower | Canada, SemBioSys Genetics Inc. | diabetes | phase1 |
| Vaccine | lettuce | Poland, Polish academy of science | hepatitis B | phase 1 |
| Vaccine | potato | USA, Arizona State University | Norwalk virus | phase 1 |
| Vaccine | spinach | USA, Thomas Jefferson University, Philadelphia | rabies | phase 1 |
| Lactoferrin | maize | France, Meristem Therapeutics | dry eye syndrome, gastro-intestinal infection | phase 1 |
| Vaccine | potato | USA, Arizona State University | diarrhoea | phase 1 |
| Vaccine | maize | USA, Arizona State University | diarrhoea | phase 1 |
| Vaccine | maize | USA, ProdiGene | diarrhoea | phase 1 |
| Alpha-Interferon | duckweed | USA, Biolex | hepatitis B | phase 1 |
| Monoclonal antibody | not announced | USA, Planet Biotechnology | reducing adverse effects of chemotherapy | phase 1 |

Fig. 17

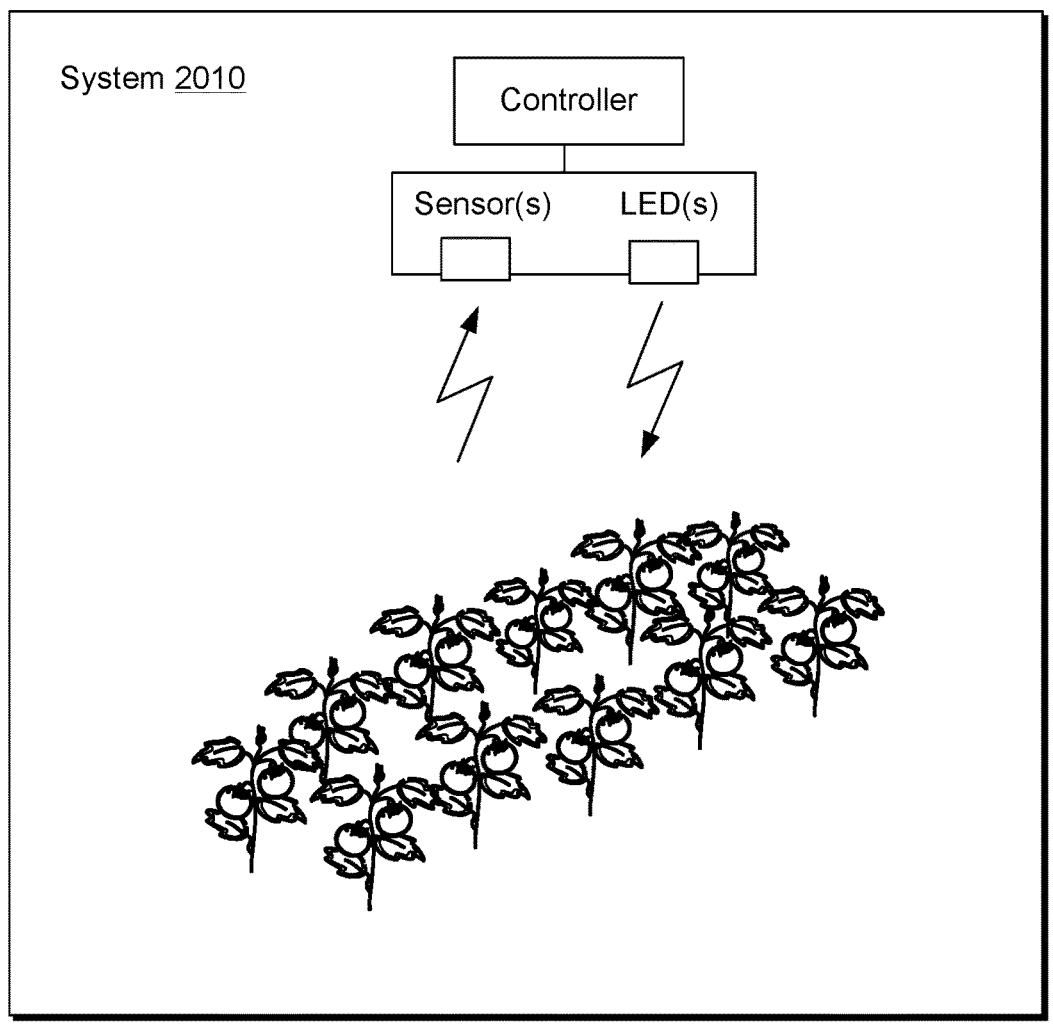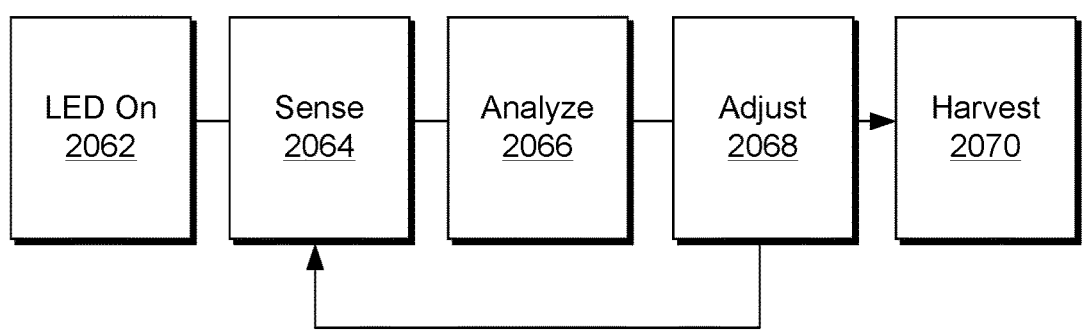
Fig. 20

THERAPEUTIC ILLUMINATION SYSTEM

RELATED APPLICATIONS

This application is a continuation of a co-pending U.S. patent application Ser. No. 14/983,578, filed 30 Dec. 2015 (issued as U.S. Pat. No. 9,913,345 on 6 Mar. 2018), which is incorporated by reference herein and that claims priority to and the benefit of a U.S. Provisional Application having Ser. No. 62/098,927, filed 31 Dec. 2014, which is incorporated by reference herein.

TECHNICAL FIELD

Subject matter disclosed herein generally relates to illumination techniques and technologies.

COPYRIGHT NOTICE

A portion of the disclosure of this patent document contains material to which a claim for copyright is made. The copyright owner has no objection to the facsimile reproduction by anyone of the patent document or the patent disclosure, as it appears in the Patent and Trademark Office patent file or records, but reserves all other copyright rights whatsoever.

BRIEF DESCRIPTION OF THE DRAWINGS

Features and advantages of the described implementations can be more readily understood by reference to the following description taken in conjunction with the accompanying drawings.

FIG. 7 illustrates examples of systems;
FIG. 9 illustrates an example of a table;
FIG. 10 illustrates an example of a table;
FIG. 11 illustrates an example of storage;
FIG. 12 illustrates an example of a system;
FIG. 17 illustrates examples of a table;
FIG. 20 illustrates an example of a system and an example of a method.

DETAILED DESCRIPTION

Figure 1:
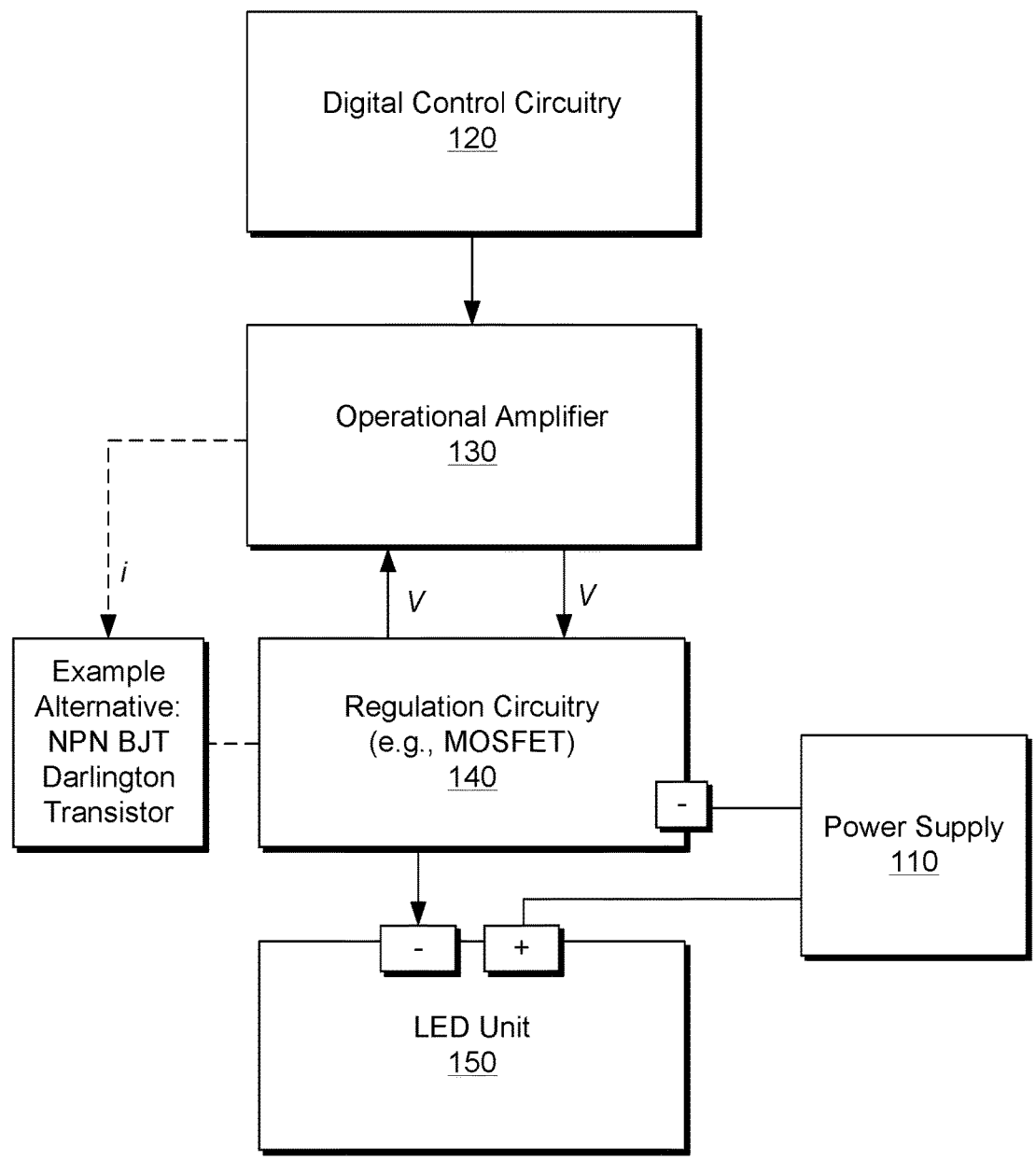
FIG. 1 illustrates an example of a system.

The following description includes the best mode presently contemplated for practicing the described implementations. This description is not to be taken in a limiting sense, but rather is made merely for the purpose of describing general principles of the implementations. The scope of the described implementations should be ascertained with reference to the issued claims.

Various types of devices can emit electromagnetic energy in a range of wavelengths from about 100 nm to about 1 mm (e.g., about 1,000,000 nm). In the foregoing range, 100 nm may correspond to ultraviolet (UV) radiation (e.g., extreme UV) and 1 mm may correspond to infrared (IR) radiation. The foregoing range includes electromagnetic radiation with a wavelength between 380 nm and 760 nm, which may be considered to be detectable by the human eye and perceived as visible light. As an example, emission may be in the range of about 800 nm to about 900 nm, in the NIR range, etc. As an example, various ranges may be of relevance to animal and plant physiology. As an example, an illumination device may include one or more types of emitters that can each emit electromagnetic energy at one or more wavelengths. For example, a laser device may emit EM energy at a particular wavelength while a light-emitting diode device may emit EM energy over a range of wavelengths, yet be specified by a single wavelength (e.g., a maximum amplitude, mean or median wavelength).

As an example, a control unit may include a camera, optionally with range into the NIR range that can automatically adapt dosage based on skin color, inflammation and/or other visual aspects, including, for example, changes from images taken in previous sessions. For example, consider a database of image information that can be accessed and used to tailor treatment, optionally in a real-time manner and/or, for example, in a pre-planned manner.

As an example, an illumination device may be used to deliver a therapy or therapies. For example, an illumination device may be a light therapy device. As to some examples of light therapy, the following article is incorporated by reference herein: Chaves M E A, Araújo A R, Piancastelli A C C, Pinotti M. Effects of low-power light therapy on wound healing: LASER×LED. An Bras Dermatol. 2014; 89 (4): 616-23. Chaves et al. concluded that light therapy can result in a "decrease in inflammatory cells, increased fibroblast proliferation, angiogenesis stimulation, formation of granulation tissue and increased collagen synthesis". Chaves et al. noted that biological effects are dependent on parameters such as wavelength and dose, which can be parameters of a treatment protocol.

As an example, low-power light therapy may be implemented for wound healing. Such a therapy may specify one or more parameters. Such a therapy may generate biological effects such as, for example, decrease of inflammatory cells, increased fibroblast proliferation, stimulation of angiogenesis, granulation tissue formation, increased synthesis of collagen, etc. Biological effects can depend on one or more parameters such as, for example, wavelength(s) and dose(s). As an example, an illumination device that can maintain a desired emission wavelength or wavelengths with respect to time may be beneficial for therapy as well as for experimental protocols. As an example, an illumination device may be used in an application other than a biological therapy (e.g., consider one or more industrial uses, etc.).

As to parameters for biological therapies, as an example, consider an illumination device that can emit EM at one or more wavelengths within a range from about 460 nm to about 1064 nm and, for example, more particularly in a range of about 630 nm to about 830 nm. As an example, a dose or doses may be measured in terms of energy per unit surface. For example, consider a single treatment (e.g., a single treatment session) where an illumination device (e.g., or devices) may deliver a dose in a range from about 0.1 J/cm² to about 90 J/cm² and, for example, more particularly from about 1 J/cm² to about 5 J/cm². The aforementioned wavelengths and doses may be applied, for example, in a wound healing therapy that aims to increase fibroblast proliferation and stimulation of angiogenesis. As an example, the aforementioned wavelengths and doses may be implemented using emitters such as lasers and/or light emitting diodes (LEDs).

Lasers can include a resonant optical cavity and different types of active media such as solid, liquid or gaseous materials, in which processes of light generation occur through the passage of an electric current. For biological therapies, potency may be in a range of about $10^{-3}$ to about $10^{-1}$ W, wavelength from about 300 nm to about 10,600 nm, pulse frequency from about 0 Hz (continuous emission) to about 5,000 Hz, pulse duration and pulse interval from about 1 milliseconds to about 500 milliseconds, total radiation from about 10 seconds to about 3000 seconds, intensity between about $10^{-2}$ and about $10^{0}$ $Wcm^{-1}$ and dose from about $10^{-2}$ to about $10^{2}$ $Jcm^{-2}$.

Various types of lasers exist such as, for example, consider solid-state lasers such as ruby lasers and yttrium-aluminum-garnet (YAG)-based lasers. As an example, a ruby laser may find use in hair removal, tattoo removal and other types of light-based therapies. As an example, a YAG-based laser may find use in hair removal, periodontal scaling, skin resurfacing, etc. As an example, a chromium doped chrysoberyl (alexandrite) laser may find use in biological therapy (e.g., dermatological therapies, etc.). As an example, a dye laser may find use in biological therapy (e.g., consider birthmark removal, etc.). For example, consider wavelengths such as 90-435 nm (stilbene), 460-515 nm (coumarin 102), 570-640 nm (rhodamine 6G), etc. As an example, a semiconductor laser may find use in biological therapy.

As an example, an LED may be a diode formed by p-n junctions (p-positive, n-negative) that, when directly polarized, causes electrons to cross the potential barrier and recombine with holes within the LED. After the spontaneous recombination of electron-hole pairs, the simultaneous emission of photons occurs. The physical mechanism by which LED emits light is spontaneous light emission. LEDs convert electrical current in a light spectrum via a process referred to as electroluminescence. An LED may operate with an output, for example, in a range of the order of milliwatts. LEDs may be set up on small chips or connected to form "light bulbs". As an example, an LED unit may include one or more LEDs, which may be the same or which may optionally differ (e.g., as to wavelength, etc.). As an example, an LED unit may be suitable for delivery of biological therapy, optionally one or more of the aforementioned laser-based therapies (e.g., depending on wavelength, dose, etc.). As an example, a controller may be operatively coupled to a LED unit that includes a plurality of LEDs where the LEDs may be controlled in unison or, for example, individually, in groups, etc. In such an example, the LEDs may be the same or they may differ.

As an example, a therapy may be specified by a protocol. As an example, an entity that markets a device may apply to a regulatory body such as the Food & Drug Administration. For example, consider a Section 510(k) premarket notification application.

As an example, so-called intense pulsed light (IPL) therapy may be indicated for use in surgical, aesthetic, and cosmetic applications. As an example, an IPL device may include flashlamps, computer-controlled power supplies, and bandpass filters to generate light pulses of prescribed duration, intensity, and spectral distribution. IPL therapy may be used to treat skin conditions such as, for example, age spots, sun-damaged skin, cutaneous lesions (such as warts, scars, and striae), benign pigmented epidermal lesions (such as freckles and melasma), and vascular lesions (such as spider veins). IPL therapy may be used to reduce undesired hair growth. As an example, IPL therapy may be implemented as a noninvasive and nonablative treatment that may target the dermis without affecting the epidermis.

To ensure safe and effective use, a clinician may aim to follow manufacturer instructions for using and properly maintaining equipment, as complications may arise when such measures are not taken. For example, the FDA has received adverse event reports of burns, blisters, scarring, and skin discolorations where one of the main factors contributing to these complications was the failure to adhere to the device's operation and maintenance instructions. For example, consider causes such as, for example, improper device calibration or failure of the user facilities to clean the device as directed in the device labeling.

As an example, a device may include calibration circuitry that may optionally take one or more actions where one or more calibration actions, issues, etc. may occur. For example, consider a lock-out until calibration is adequate. As an example, a device may include communication circuitry that can communicate one or more calibration related messages. As an example, a device may include calibration circuitry that may optionally take one or more actions in order to communicate to a user (e.g., locally and/or remotely), for example, that one or more types of maintenance may be performed, etc. (e.g., consider to calibrate, to replace one or more Field Replaceable Units (FRUs), etc.).

As an example, a control unit may include survey circuitry that calls for a survey and answers to the survey prior to being able to deliver a therapy. For example, consider a survey implemented via a touchscreen where a clinician and/or a patient may answer the survey's questions. Such questions may include, for example, "is skin appearance natural" or "due to intentional tanning, unintentional sun exposure, or any other reason". Such questions may help assess dosage, wavelength, etc. as light can react differently on different skin colors. For example, to treat the same condition, clinicians may use different levels of light energy for patients with different skin colors. As another example, a survey may include a question as to medication(s) a patient may be taking. For example, consider a survey that questions whether a patient is taking a medication that causes photosensitivity. If affirmative, the clinician may adjust treatment or avoid treatment, for example, for a number of hours, days, etc.

FIG. 1 shows an example of a system 100 that includes a power supply 110, digital control circuitry 120, operational amplifier circuitry 130, regulation circuitry 140 (e.g., MOSFET, NPN BJT Darlington transistor, etc.), and an LED unit 150. In the example of FIG. 1, the digital control circuitry 120 can include an output that is operatively coupled to an input of the operational amplifier circuitry 130 and the operational amplifier circuitry 130 can include an output that is operatively coupled to the regulation circuitry 140 and the operational amplifier circuitry 130 can include another input that is operative coupled to the regulation circuitry 140. In such an example, a control loop may be established where the regulation circuitry 140 can regulate power to the LED unit 150, for example, as supplied via the power supply 110. As an example, such a control loop may be a current control loop that controls current to the LED unit 150 (e.g., or optionally another type of unit).

As an example, a method can include outputting a voltage from the digital control circuitry 120 where at least a portion of the voltage is received by one of the inputs of the operational amplifier circuitry 130. In such an example, the method can include outputting via the operational amplifier circuitry 130 an amplified voltage via its output, which may be received, at least in part, by the regulation circuitry 140.

Figure 2:
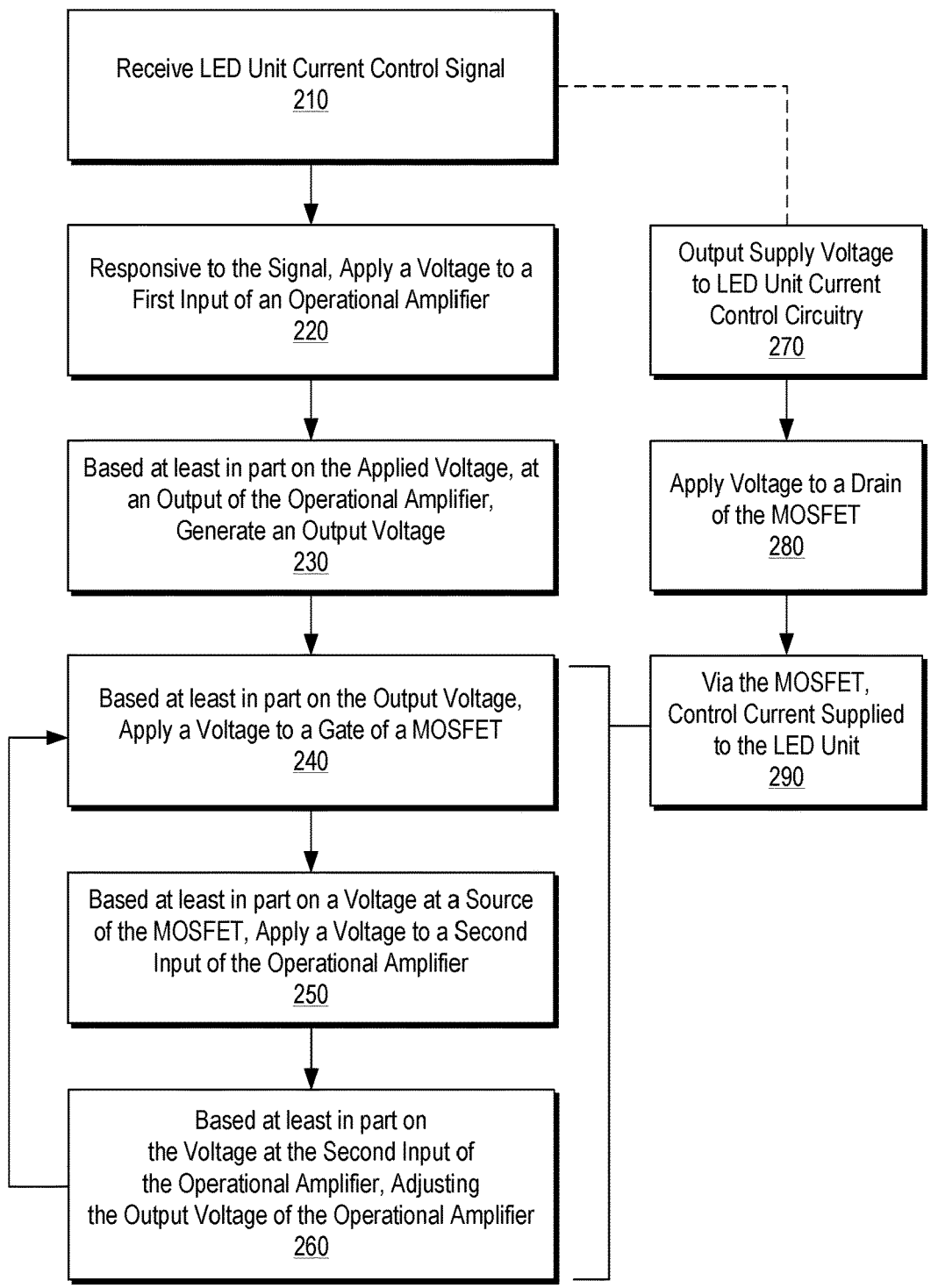
FIG. 2 illustrates an example of a method.

FIG. 2 shows an example of a method 200 that includes a reception block 210 for receiving an LED unit current control signal, an application block 220 for, responsive to the signal, applying a voltage to a first input of an operational amplifier, a generation block 230 for generating an output voltage at an output of the operational amplifier based at least in part on the applied voltage, an application block 240 for applying a voltage to a gate of a MOSFET based at least in part on the output voltage, an application block 250 for applying a voltage to a second input of the operational amplifier based at least in part on a voltage a source of the MOSFET and an adjustment block 260 for adjusting the output voltage of the operational amplifier based at least in part on the voltage at the second input of the operational amplifier. As shown in the example of FIG. 2, the adjustment block 260 may continue to the application block 240. For example, a control loop may be established via various blocks such as the blocks 240, 250 and 260 of the method 200.

In the example of FIG. 2, the method 200 can include an output block 270 for outputting a supply voltage to LED unit current control circuitry, an application block 280 to apply a voltage to a drain of the MOSFET and a control block 290 to, via the MOSFET, control current supplied to the LED unit.

As an example, a system such as the system 100 of FIG. 1 may implement, at least in part, the method 200 of FIG. 2.

Figure 3:
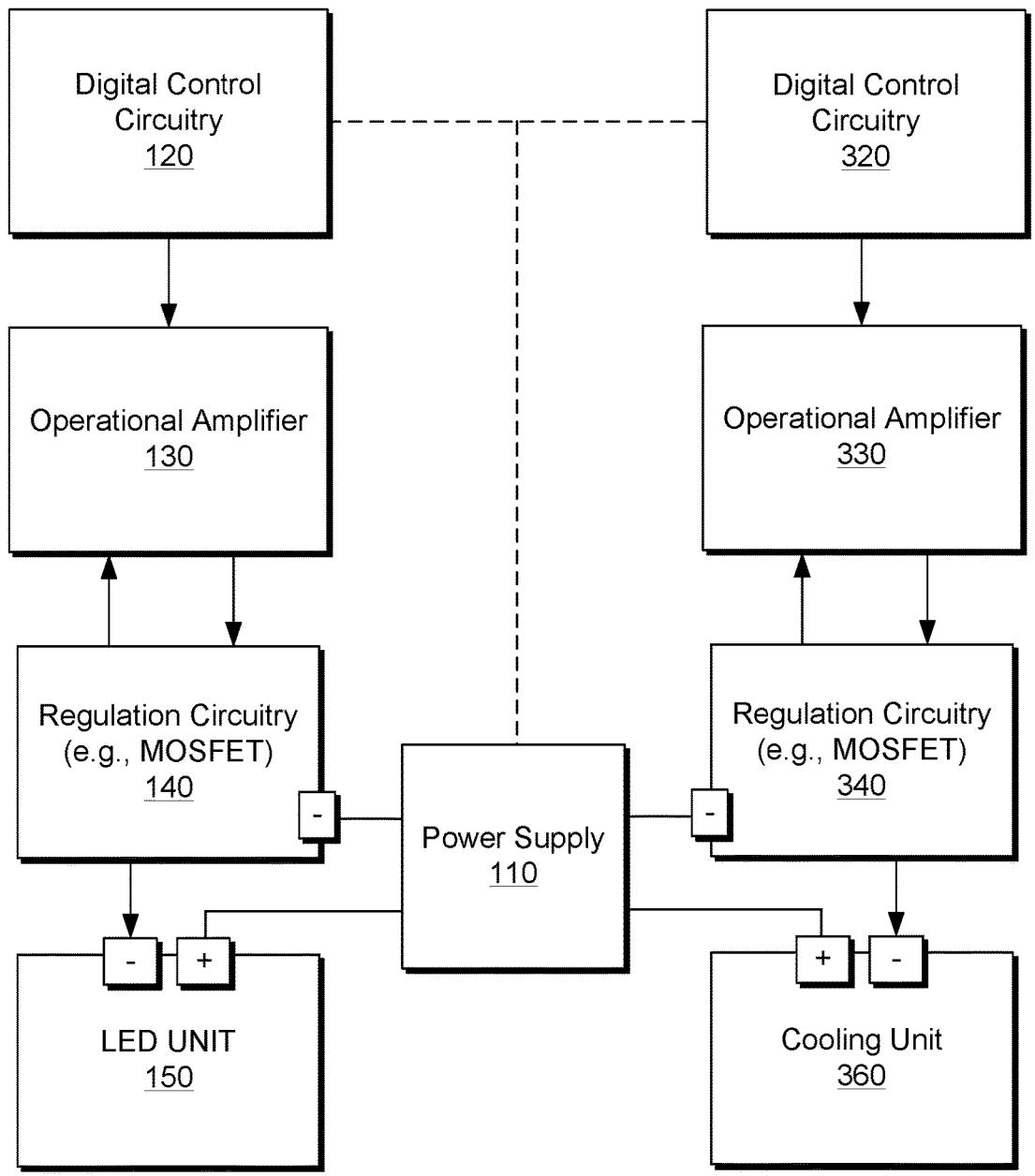
FIG. 3 illustrates an example of a system.

FIG. 3 shows an example of a system 300 that includes the system 100 of FIG. 1 and digital control circuitry 320, an operational amplifier 330, regulation circuitry 340 (e.g., a MOSFET, a NPN BJT Darlington transistor, etc.), and a cooling unit 360. As shown, the power supply 110 may supply power to the cooling unit 360 where regulation of the cooling unit 360 may be achieved at least in part via the regulation circuitry 340.

As an example, the system 300 can provide for converting digital to analog. For example, a system can include a LED unit socket that is operatively coupled to LED supply circuitry. In such an example, the LED supply circuitry can include a digital to analog converter, an operational amplifier operatively coupled to an analog output of the digital to analog converter, and a metal-oxide-semiconductor field-effect transistor that includes a gate operatively coupled to an output of the operational amplifier, a source operatively coupled to an input of the operational amplifier and a drain operatively coupled to the LED unit socket.

Figure 4:
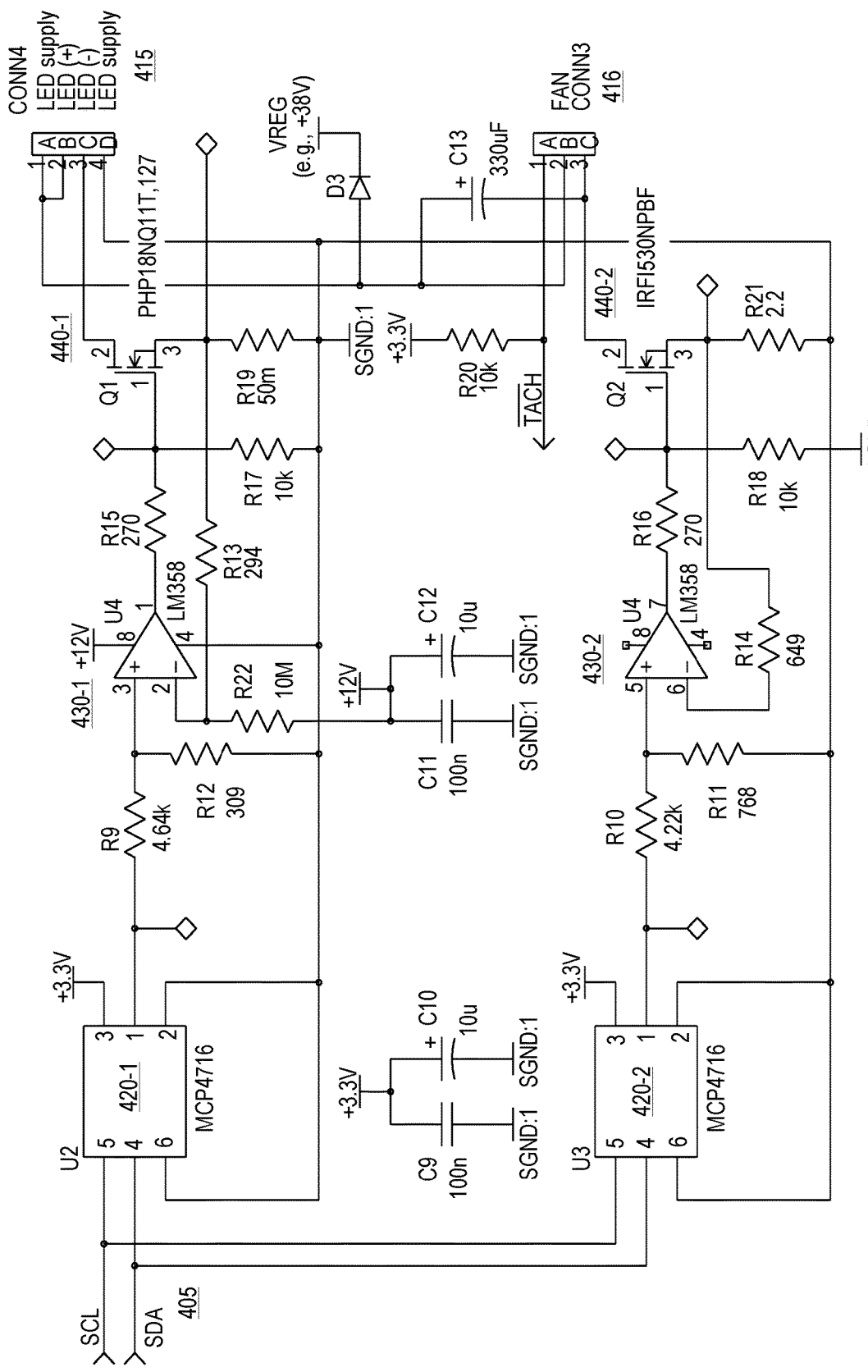
FIG. 4 illustrates an example of a system.

FIG. 4 shows an example of a system 400 that includes various components. As shown in FIG. 4, the system 400 includes a digital interface 405 that may receive a clock signal (SCL) and a data signal (SDA). As an example, the digital interface 405 may be an I²C interface. In such an example, signals may be received by the system 400 where an individual signal may be addresses (e.g., include address information) such that the signal is processed by a particular component that has an assigned address. For example, the system 400 includes a component 420-1 and a component 420-2 where the component 420-1 may include an address that differs from an address of the component 420-2. As an example, the component 420-1 may be associated with control of a LED unit and the component 420-2 may be associated with control of a cooling unit. As an example, the component 420-1 and the component 420-2 may output a voltage at an output (e.g., with respect to ground) based at least in part on a signal received at an input (e.g., a signal interface).

As shown in the example of FIG. 4, the system 400 can include an operational amplifier 430-1 and an operational amplifier 430-2. As shown, the operational amplifier 430-1 may receive, at an input (e.g., directly or indirectly), a voltage output by the component 420-1 and the operational amplifier 430-2 may receive, at an input (e.g., directly or indirectly), a voltage output by the component 420-2.

As shown in the example of FIG. 4, the operational amplifier 430-1 and the operational amplifier 430-2 may form in part respective control loops for control of an LED unit and for control of a cooling unit, respectively. For example, the operational amplifier 430-1 may be operatively coupled to a MOSFET 440-1 associated with an LED unit interface 415 and the operational amplifier 430-2 may be operatively coupled to a MOSFET 440-2 associated with a cooling unit interface 416.

As an example, the system 400 may include an interface that can receive a signal from a cooling unit. For example, a cooling unit can include circuitry that can output a tachometer signal (e.g., a speed signal, rpm, etc.). In such an example, the interface may communicate the signal from the cooling unit to a controller. In such an example, the controller may include an interface that can output signals to the component 420-1 and the component 420-2. As an example, the controller may output a signal to the component 420-2 based at least in part on a signal from a cooling unit (e.g., a speed signal, etc.).

In FIG. 4, various values are shown for components such as resistors, connectors, etc. such values are given as examples. For example, a power supply may be rated to provide DC power at about 38 V. As an example, an amount of current to an LED unit may be specified to have a maximum value of about 4 A. As an example, an operational amplifier may be supplied with a voltage of about 12 VDC. As an example, a component such as the component 420-1 and/or the component 420-2 may be supplied with a voltage of about 3 V to about 5 V for operation of circuitry therein (e.g., to perform one or more functions associated with input and/or output).

As an example, a power supply may be operated at a relatively small voltage difference from a voltage supplied to one or more LED units. For example, consider a voltage supplied to an LED unit at about 17 V where a power supply is operated at about 18 V. Such an approach may aim to improve efficiency of a system.

As an example, a bus may be operatively coupled to the system 400. In such an example, the bus may be a two-wire bus or other type of bus. As an example, a bus may be a bus capable of communicating address information, for example, such that signals are received by an appropriate component. As an example, a component or components may include interface circuitry that can operatively couple to a bus, for example, for receipt and/or transmission of information.

In the example of FIG. 4, a resistor R22 can be included (see, e.g., the operational amplified 430-1), which may provide for input bias compensation. Such an approach may reduce input to the MOSFET 440-1, for example, R22 in conjunction with R13 can establish a slight, positive threshold voltage at the inverting terminal of the operational amplifier 430-1 such that an input voltage at the non-inverting terminal is to exceed this threshold voltage for the output of the operational amplifier 430-1 to present a non-zero voltage (e.g., possibly with a small offset voltage) to the MOSFET 440-1.

In the example of FIG. 4, a capacitor C13 can be included as a fan voltage stabilizing capacitor. For example, a brushless DC motor can use electronic switching circuits to drive a fan. Such circuitry can be provided with a relatively stable, low impedance DC voltage source; however, where a driving circuit implemented includes a high impedance current source, a capacitor such as the capacitor C13 can help to stabilize voltage across a fan and, for example, can buffer the fans varying current demands, which may average out to a value set by the current source.

In the example of FIG. 4, the components 420-1 and 420-2 may be digital to analog converters. For example, consider an 8-bit, a 10-bit, a 12-bit, etc. voltage output digital to analog converter (DAC) such as, for example, a DAC marketed by Microchip Technology Inc. (Chandler, Ariz.) (e.g., MCP4706, MCP4716, MCP4726, etc.). As an example, a DAC can include EEPROM and an I²C interface.

Figure 5:
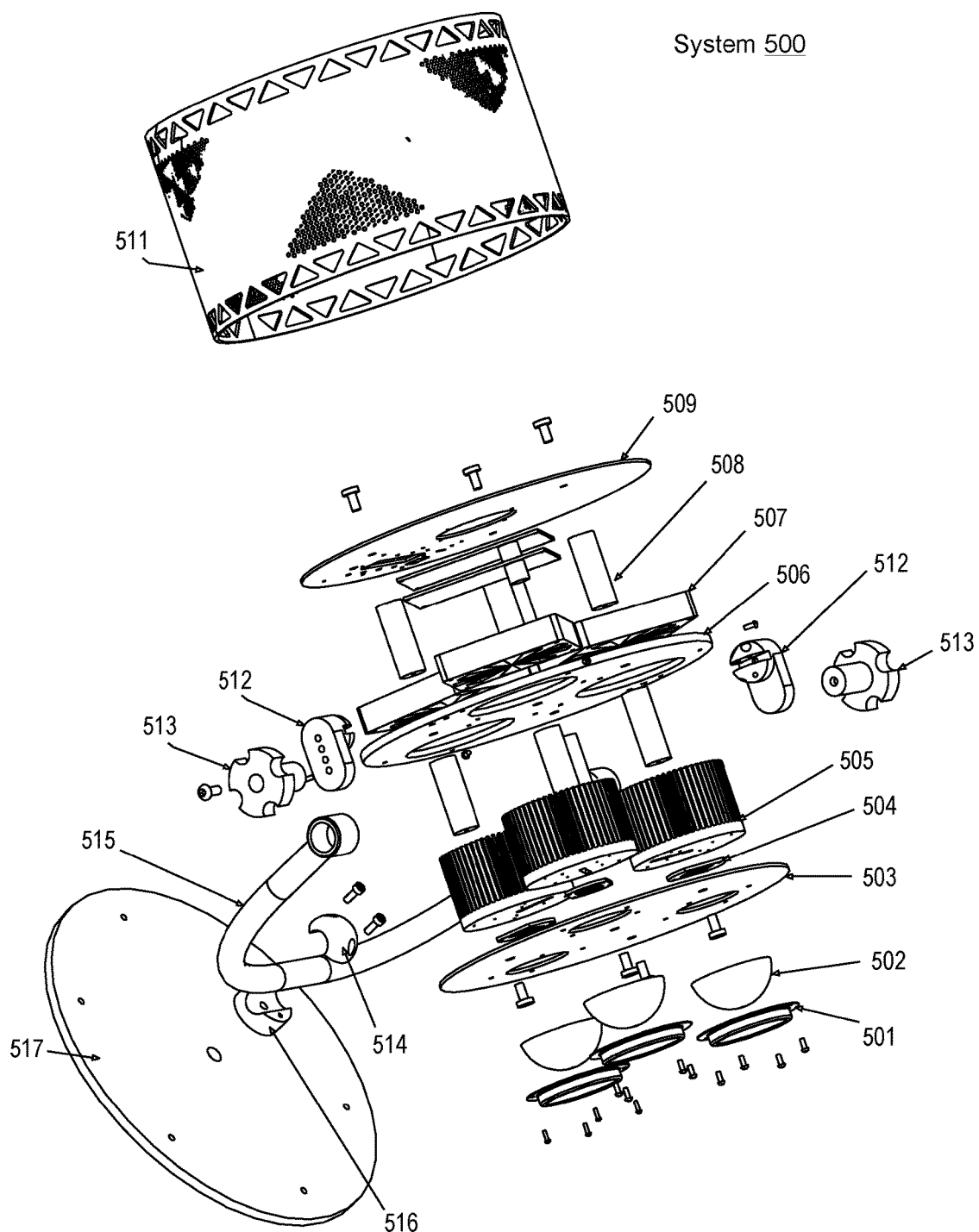
FIG. 5 illustrates an example of a system.

FIG. 5 shows an example of a system 500 that includes one or more lens retaining rings 501, one or more lenses 502, a lens plate 503, one or more LED modules 504, one or more heat sinks 505, a fan plate 506, one or more fans 507, one or more spacers 508, a circuit plate 509, an optional heat sink top cap, a lamp skirt 511, one or more armature mounts 512, one or more clamping knobs 513, a stand adapter cap 514, an armature weldment 515, a stand adapter mount 516, a stand base plate 517, U/I circuitry 518, and I/O circuitry 519. As an example, the circuit plate 509 may include MOSFET circuitry that can mount to the fan plate 506, for example, between individual fans 507 and the fan plate 506.

As to cooling, a system may include one or more fluid cooling components. For example, a fan may move air as a fluid. As another example, a cooling unit may include a closed fluid loop or loops. In such an example, a pump or other mover may cause fluid to flow in the loop or loops. As an example, a system may include one or more types of cooling units.

Figure 6:
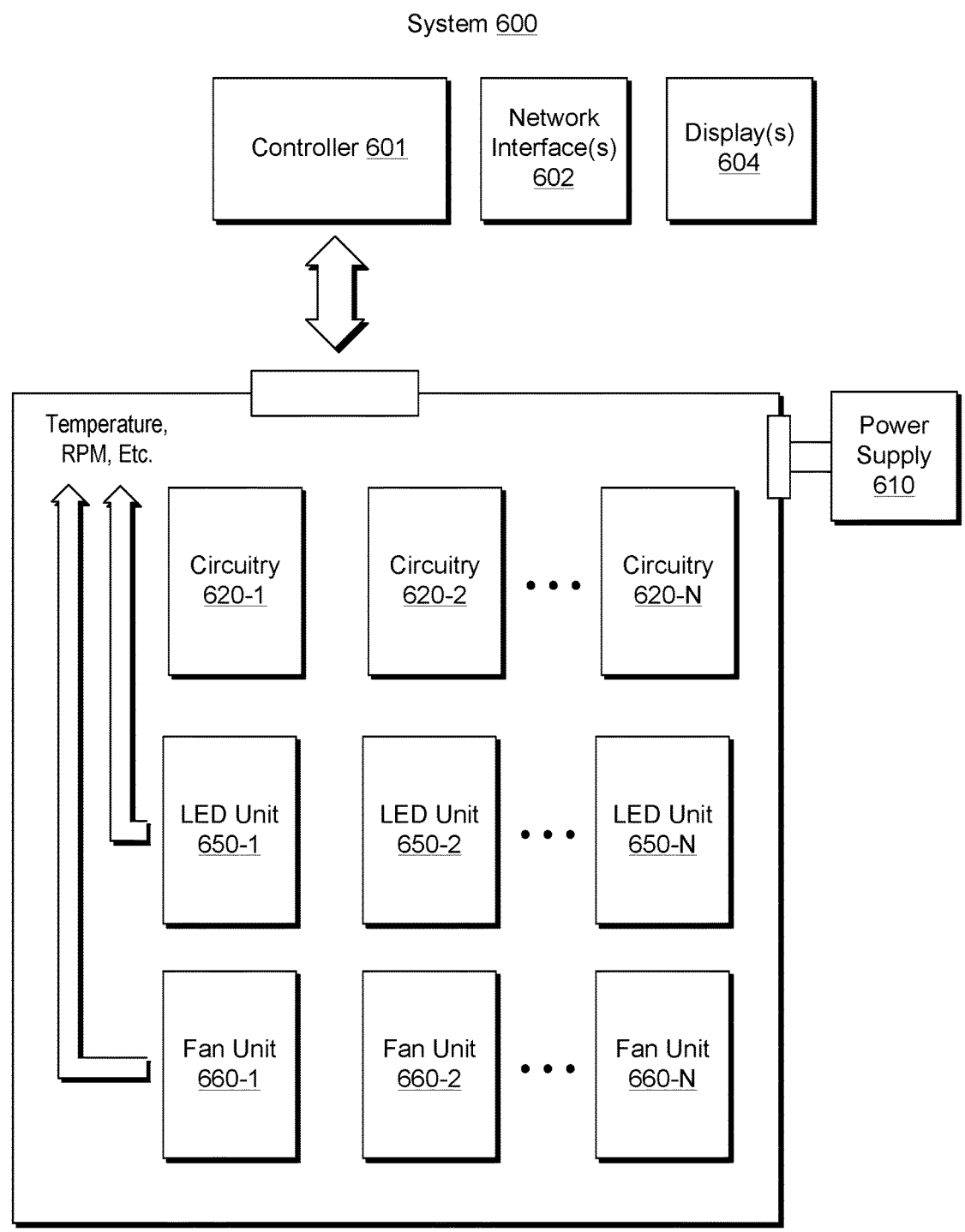
FIG. 6 illustrates an example of a system.

FIG. 6 shows an example of a system 600 that includes a controller 601, one or more network interfaces 602 and one or more displays 604. As shown in the example of FIG. 6, the controller 601 may interface with a system such as the system 500, which may include circuitry such as the circuitry 620-1, 620-2 to 620-N, one or more LED units such as the LED units 650-1, 650-2 to 650-N, and one or more cooling units such as the fan units 660-1, 660-2 to 660-N. In the example of FIG. 6, a power supply 610 is shown, which may supply power to various circuitry, LED units, cooling units, etc.

In the example of FIG. 6, information such as, for example, temperature, fan speed, etc. may be communicated to the controller 601. As an example, a signal or signals from the fan connector 416 of FIG. 4 may be transmitted to the controller 601.

FIG. 7 shows an example of a system 710, an example of a system 750 and an example of a method 760. In the system 710, an assembly may be positioned with respect to an individual to deliver a therapy. As shown, the assembly may be positioned a distance ($\Delta z$) from a surface of the individual. As an example, the assembly may include a sensor or sensors that may sense a distance or distances. As an example, where the assembly includes a group of three radiation units, the units may be arranged such that they emit radiation that may be characterized by a field-of-view (FOV). As an example, the FOV may depend on distance. As an example, a system may include a mechanism that can adjust a distance of an assembly to a surface of an individual, for example, by moving the assembly, the individual or the assembly and the individual. As an example, a dose may depend on distance. As an example, a system may adjust a dose by adjusting a distance.

As an example, an assembly may include one or more lenses. As an example, a lens may be an adjustable lens that can, for example, control a FOV of a unit that emits radiation (e.g., an LED unit, etc.).

As shown, the system 750 includes an assembly that may be positioned with respect to an individual. As shown, the assembly may include one or more LED units and one or more temperature sensors. The system 750 may include a controller that can control emission by the one or more LED units and sensing by the one or more temperature sensors.

In FIG. 7, the method 760 can include a LED off control block 762 for switching off one or more LED units, a temperature sense block 764 for sensing temperature, an LED on control block 766 for switching on one or more LED units, a temperature sense block 768 for sensing temperature, a determination block 770 for determining a temperature difference (e.g., between T1 and T2, etc.) and an optional compensation block 772 for compensating one or more temperatures based at least in part on a determined temperature difference.

As an example, a method can include taking an initial temperature reading with a light off, turning the light on and taking a subsequent temperature reading, determining a difference between the initial temperature reading and the subsequent temperature reading, and storing the difference. Such a method may include determining one or more temperatures based on one or more subsequent temperature readings, for example, by subtracting out the aforementioned stored difference.

Figure 8:
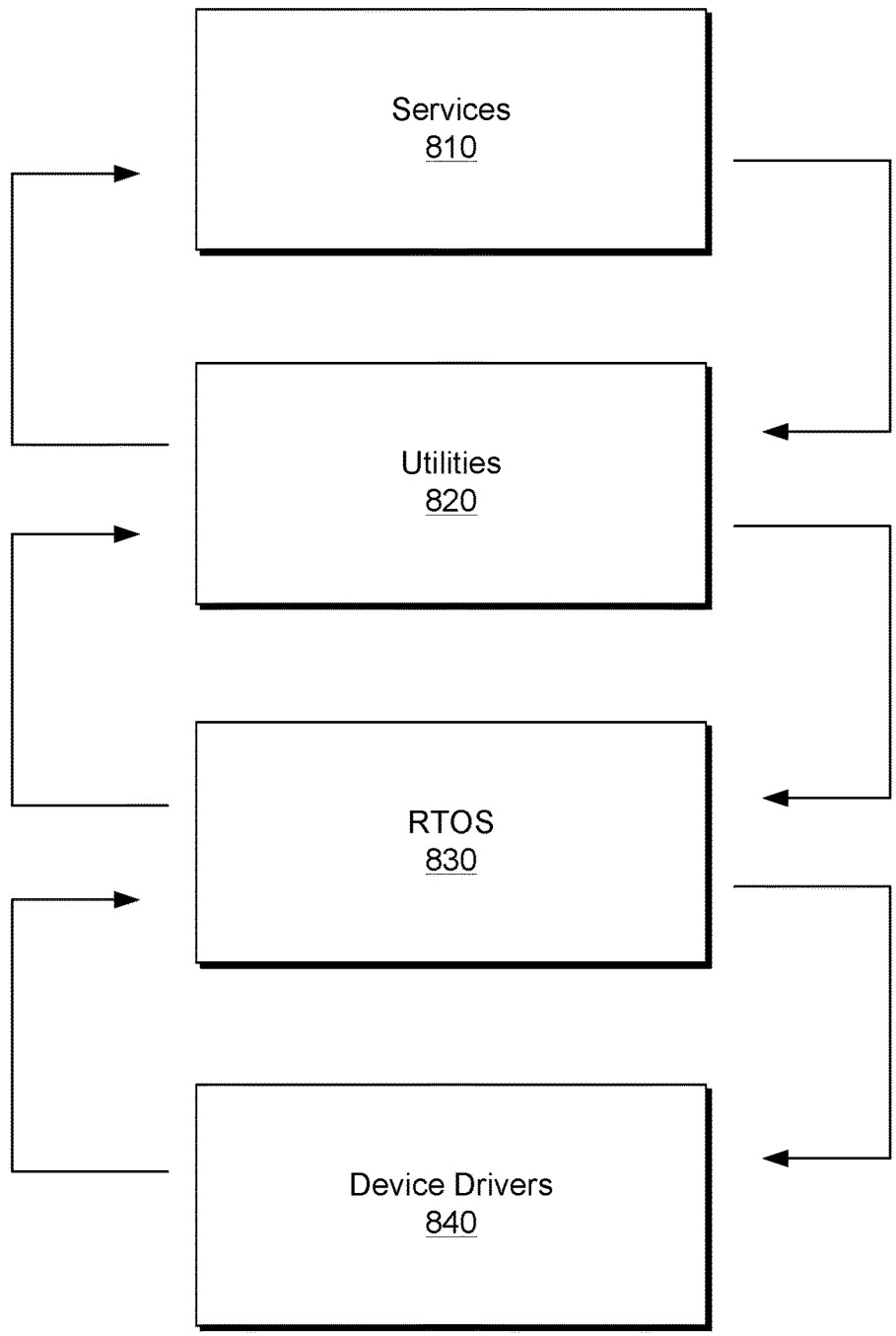
FIG. 8 illustrates an example of a system.

FIG. 8 shows an example of a system 800 that includes various layers including a services layer 810, a utilities layer 820, a real-time operation system (RTOS) layer 830 and a drivers layer 840. Such a system may be referred to as an architecture. As an example, the system 600 may operate according to an architecture that includes layers such as the layers 810, 820, 830 and 840.

FIG. 9 shows an example of a table 900 that includes a column with examples of drivers and associated equipment (e.g., components, devices, etc.). As an example, the drivers layer 840 of FIG. 8 may include drivers such as one or more of the drivers of the driver column of the table 900 of FIG. 9.

FIG. 10 shows an example of a table 1000 that includes a column with examples of utilities and associated equipment (e.g., components, devices, etc.). As an example, the utilities layer 820 of FIG. 8 may include utilities such as one or more of the utilities of the utility column of the table 1000 of FIG. 10.

FIG. 11 shows an example of storage 1100 (e.g., memory, etc.) that can store information. As shown, the storage 1100 can store information such as configuration information, LED associated information, fan associated information, timeout information, temperature information, firmware version information, user information, warning level information, error level information, user interface information, ETHERNET interface information, WIFI wireless information (e.g., and/or BLUETOOTH, etc.), networking information, machine control information, machine status information, logging information, and other information (e.g., consider equipment usage, authorizing operator, patient identification, etc.).

As an example, a system may include cellular network circuitry such as, for example, CDMA, GSM, etc. In such an example, the system may communicate via a cellular network. As an example, a system can include a SIM chip or card. As an example, a system may automatically transmit information to one or more numbers associated with one or more cellular networks. As an example, a system may operatively couple to the Internet via a cellular network.

FIG. 12 shows examples of services 1200 including a bootstrap service 1210, a condition service 1220, a thermal management service 1230 and a user service 1240. As an example, the services layer 810 of FIG. 8 may include services such as one or more of the services 1200 of FIG. 12.

Figure 13:
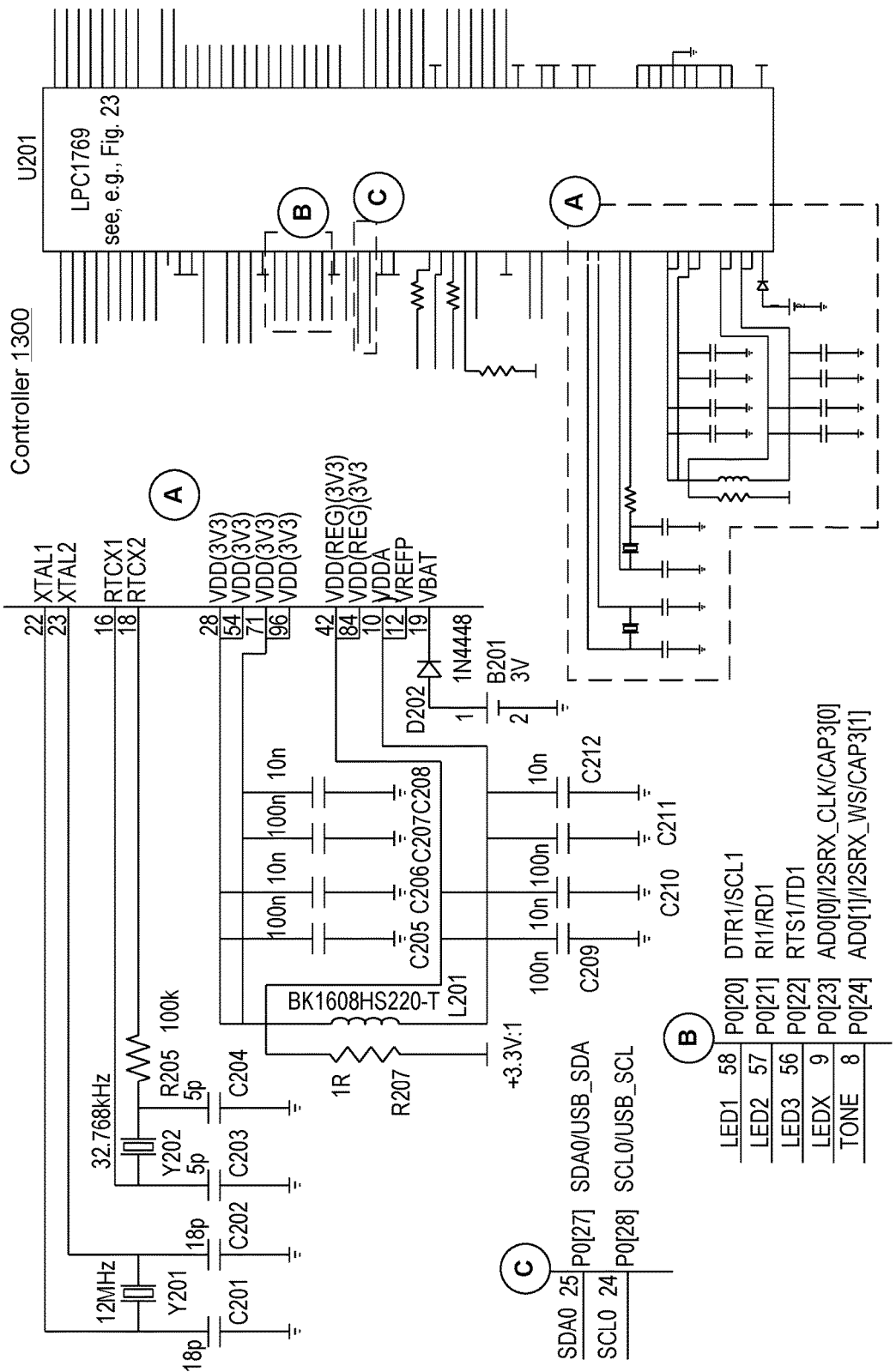
FIG. 13 illustrates an example of a processor.
Figure 23:
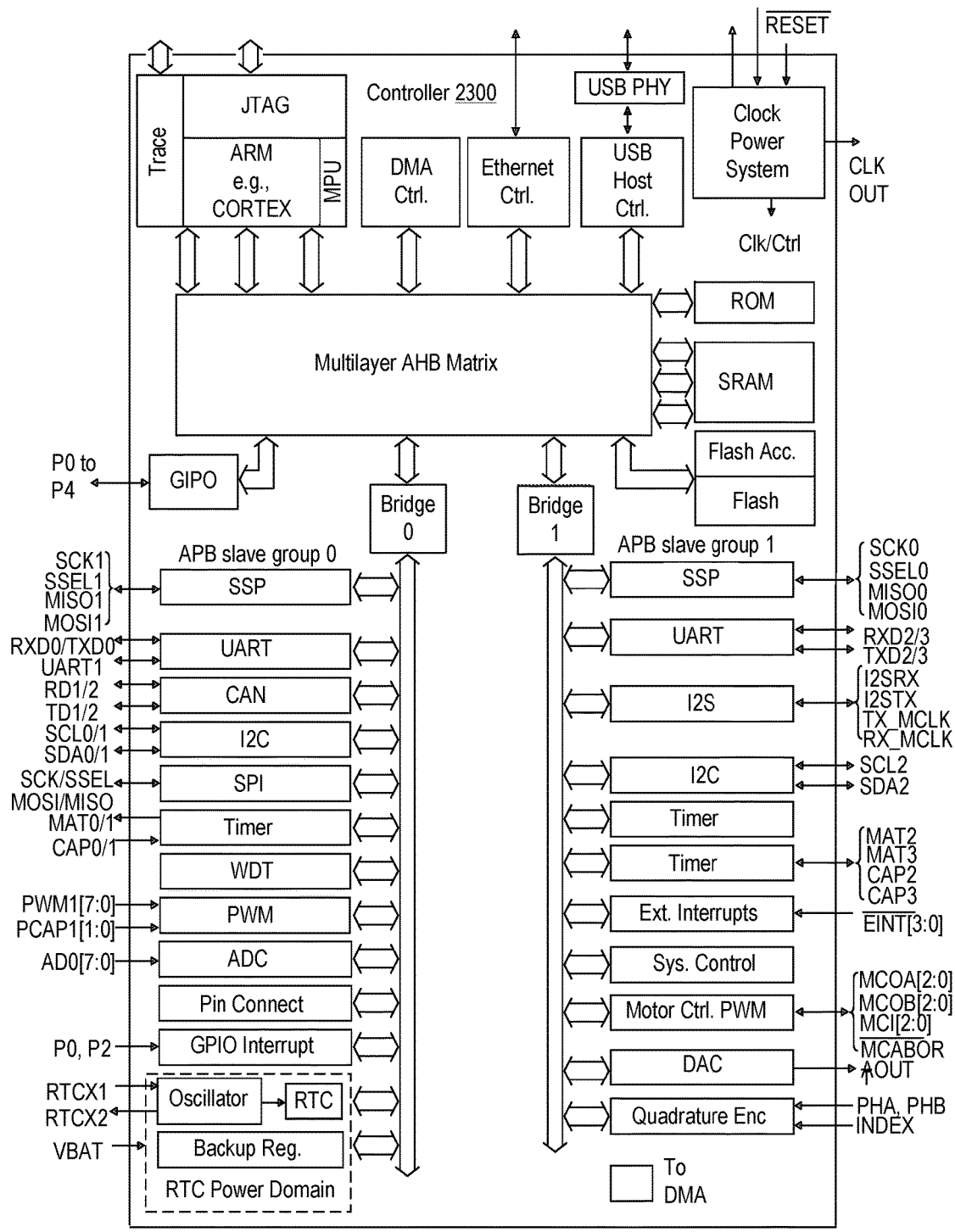
FIG. 23 illustrates an example of a controller.

FIG. 13 illustrates an example of a controller 1300 that includes a processor (see, e.g., the example of FIG. 23). In the example of FIG. 13, portions of circuitry are illustrated with examples of components. One portion is labeled A, another portion is labeled B and yet another portion is labeled C.

Figure 14:
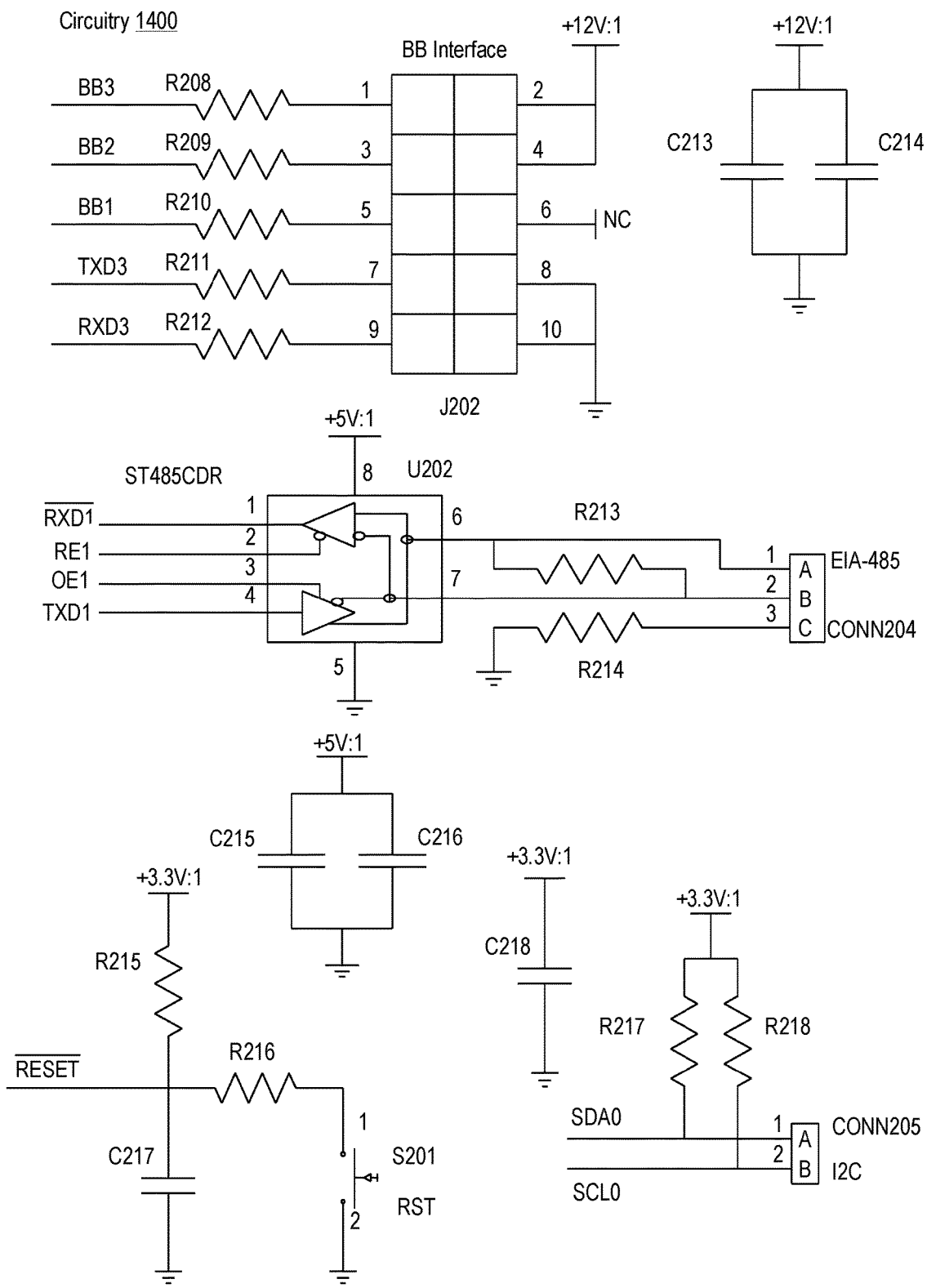
FIG. 14 illustrates examples of circuitry.

FIG. 14 illustrates examples of circuitry 1400 along with various connections. As an example, various connections of the circuitry 1400 may be operatively coupled to a controller of a system (see, e.g., FIG. 13 and FIG. 23).

Figure 15:
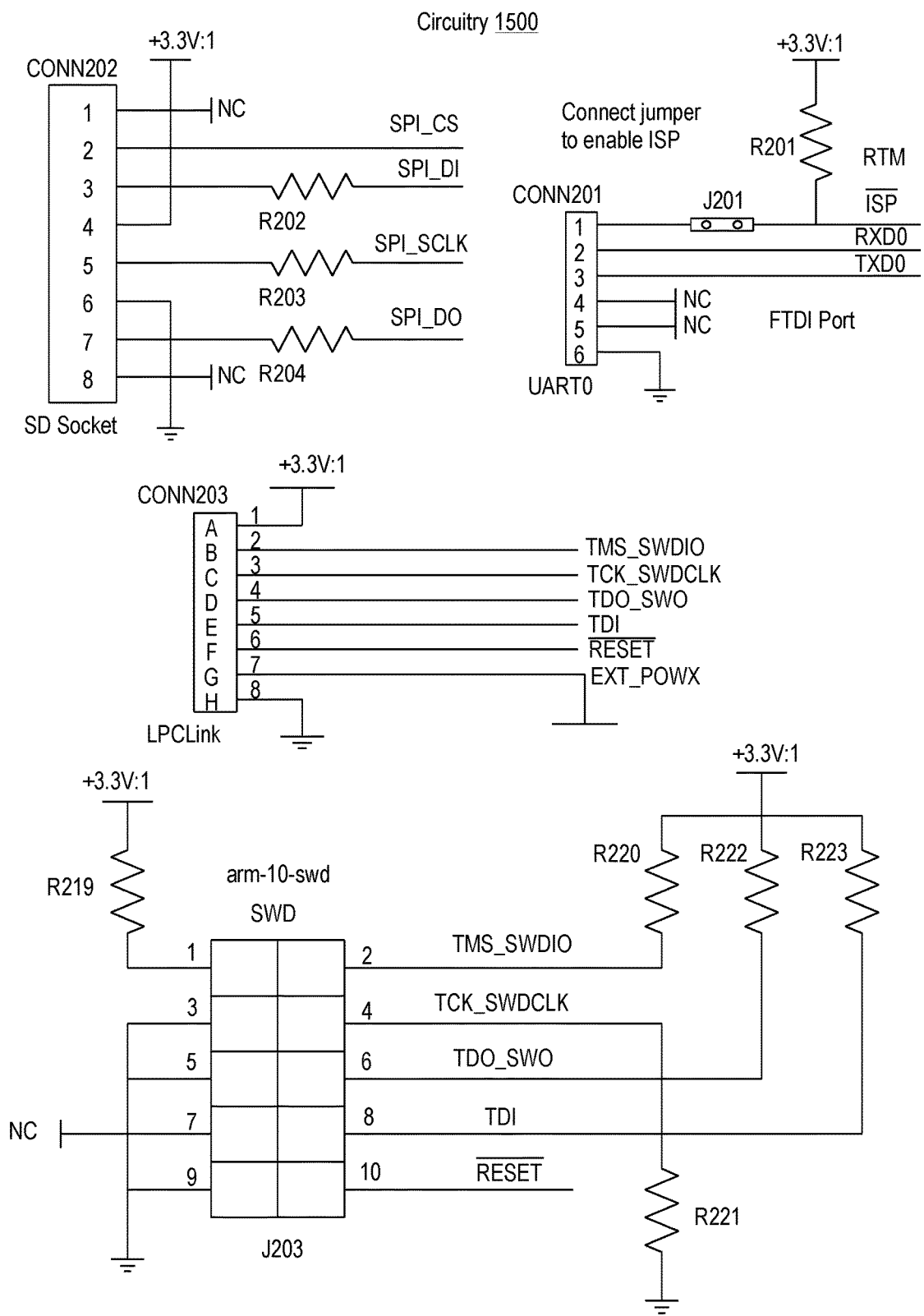
FIG. 15 illustrates examples of circuitry.

FIG. 15 illustrates examples of circuitry 1500 along with various connections. As an example, various connections of the circuitry 1500 may be operatively coupled to a controller of a system (see, e.g., FIG. 13 and FIG. 23).

Figure 16:
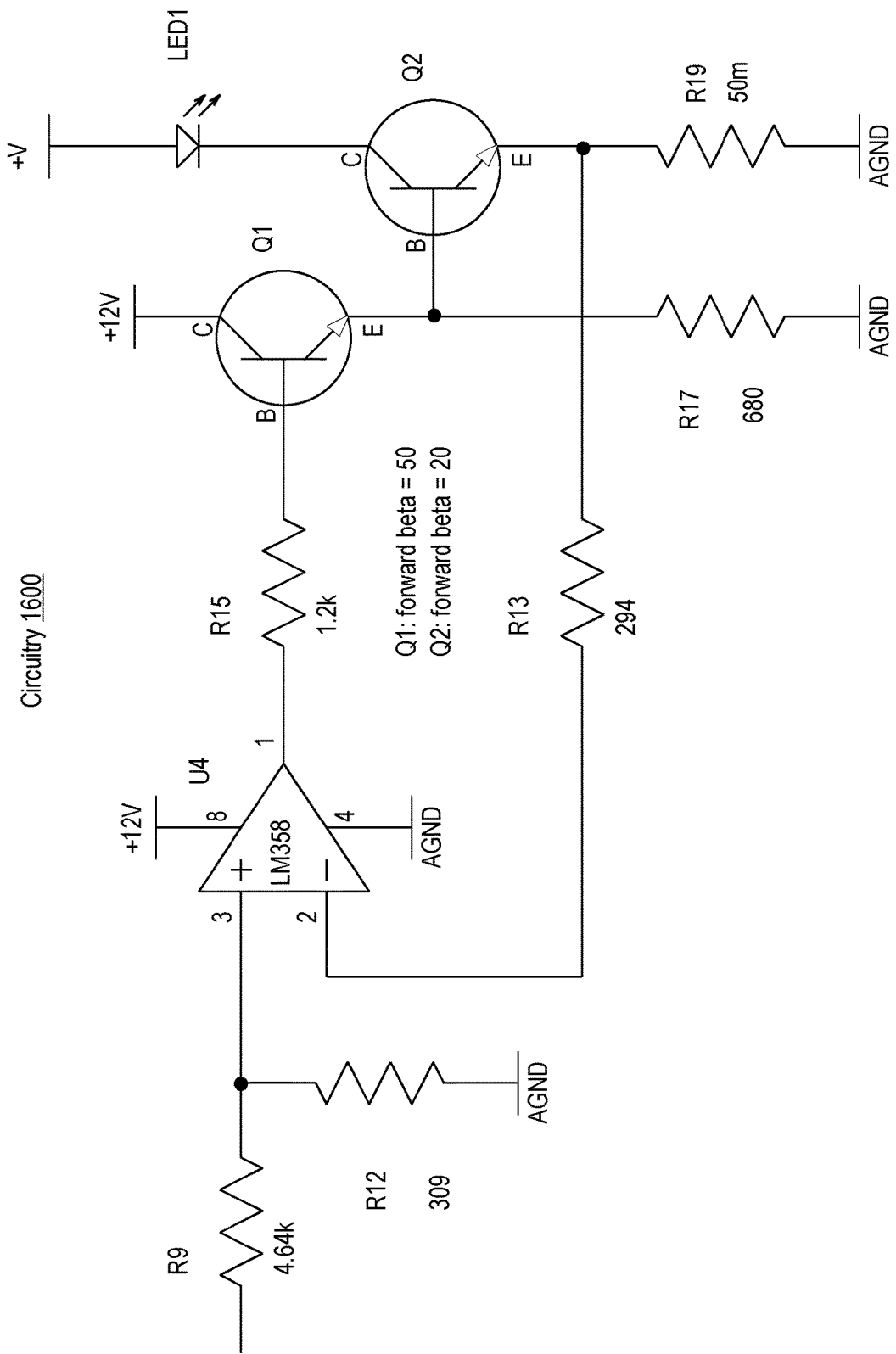
FIG. 16 illustrates an example of circuitry.

FIG. 16 illustrates an example of circuitry 1600. As shown, the circuitry 1600 includes a loop with an operational amplifier. Such a loop may act to regulate power supplied to one or more LEDs, for example, as one or more LED units. As an example, circuitry such as the circuitry 1600 may be employed to regulate power supplied to another component, assembly, etc. As an example, circuitry such as the circuitry 1600 may be appropriately configured to regulate power supplied to a cooling unit or cooling units (e.g., one or more fan units, etc.).

As an example, voltage drop of an LED can depend on the particular LED and an amount of current flowing through the LED. For example, consider a particular LED that varies by about two volts. In such an example, to minimize the power losses in a control circuit, a supply voltage may be a minimal amount above the maximum voltage drop of the LED (e.g., consider an amount of about a volt). As an example, power loss in a control transistor may be defined as the product of driving current and voltage drop across the transistor. As an example, for a power transistor to be able to control current, it can operate in an "active mode" (e.g., as opposed to a "saturation mode". As an example, per the datasheet for the PHP18NQ11T MOSFET, consider the drain current versus drain-to-source voltage for different values of gate-to-source voltage, where it can be seen that a drain current of over about 5 A can be obtained with a drain-to-source voltage of less than about 0.5 V. In such an example, the gate-to-source voltage may be about 6 V, which, as an example, may be about half of what an operational amplifier may deliver. As an example, consider an LED (e.g., an LED unit with multiple LEDs) dropping about 20 V and using a current of about 5 A, with a control MOSFET having minimum drain-to-source voltage drop of about 0.5V—active mode. In such an example, a supply voltage may be about 21 V, where total power in may be calculated as 21 V*5 A to equal about 105 W. Further, consider power delivered to the LED (e.g., an LED unit with multiple LEDs) to be about 20 V*5 A to equal about 100 W. In such an example, power "lost" to the control MOSFET may be estimated to be about 1 V*5 A to equal about 5 W. Given the foregoing examples of power, efficiency or percentage of power may be calculated as being delivered to the LED (e.g., an LED unit with multiple LEDs) to be about 100 W divided by about 105 W to equal about 95.2% (e.g., efficiency greater than about 90% and optionally greater than about 95%). As an example, in a system, a supply voltage value may be chosen to be, for example, about 1 V above a maximum voltage drop of a supplied unit such as, for example, an LED unit. While a value of 1 volt is given for the example numbers, above, a percentage may be used to determine an "excess" amount of voltage, etc. As explained, circuitry that includes a control MOSFET may provide good efficiency and account for small voltage drops in wiring, etc. As an example, circuitry such as the circuitry of FIG. 16 may be employed, again, in a manner to provide good efficiency (e.g., to operate with a power source that outputs a voltage about a volt above that of a unit to be powered).

As an example, a system can include circuitry to implement security. For example, a system may include circuitry that can implement security via software, hardware or software and hardware. As an example, a system can implement encryption that can encrypt information, which may be stored and/or transmitted. As an example, a system can include circuitry for wireless and/or wired security. As an example, a system may implement AES and/or PKI types of security. As an example, a system may circuitry that can accept signed and encrypted software upgrades via a network (e.g., online, etc.), through a media card, etc. As an example, dual-factor security may be accomplished thorough use of one or more PUF (physical unclonable function) hardware modules.

A PUF may implement challenge—response authentication. For example, when a physical stimulus is applied to a PUF structure, it can react in an unpredictable (but repeatable) way due to interaction of the stimulus with the physical microstructure (e.g., PUF structure). An applied stimulus may be called a challenge and a reaction of a PUF may be called a response. A specific challenge and its corresponding response together form a challenge—response pair or CRP. A PUF structure's (e.g., device with an embedded PUF or PUFs, etc.) identity is established by properties of the structure itself. As this structure is not directly revealed by the challenge-response mechanism, such an approach is resistant to spoofing attacks. As an example, a PUF may be constructed in hardware proportional to the number of challenge and response bits.

As an example, a controller (e.g., consider a NXP1769 controller with an associated microprocessor, etc.) may include on-board flash and RAM that may be locked (e.g., accessible via authorization). Such an approach may protect against unauthorized cloning.

As an example, a system may include circuitry that can load encrypted software. As an example, a system may include circuitry that can encrypt wireless communications. As an example, a system may include circuitry such that access to one or more external interfaces, serial ports, ETHERNET interfaces, etc. only allowed after proper password authentication (e.g., crypto-key identification, etc.).

Figure 18:
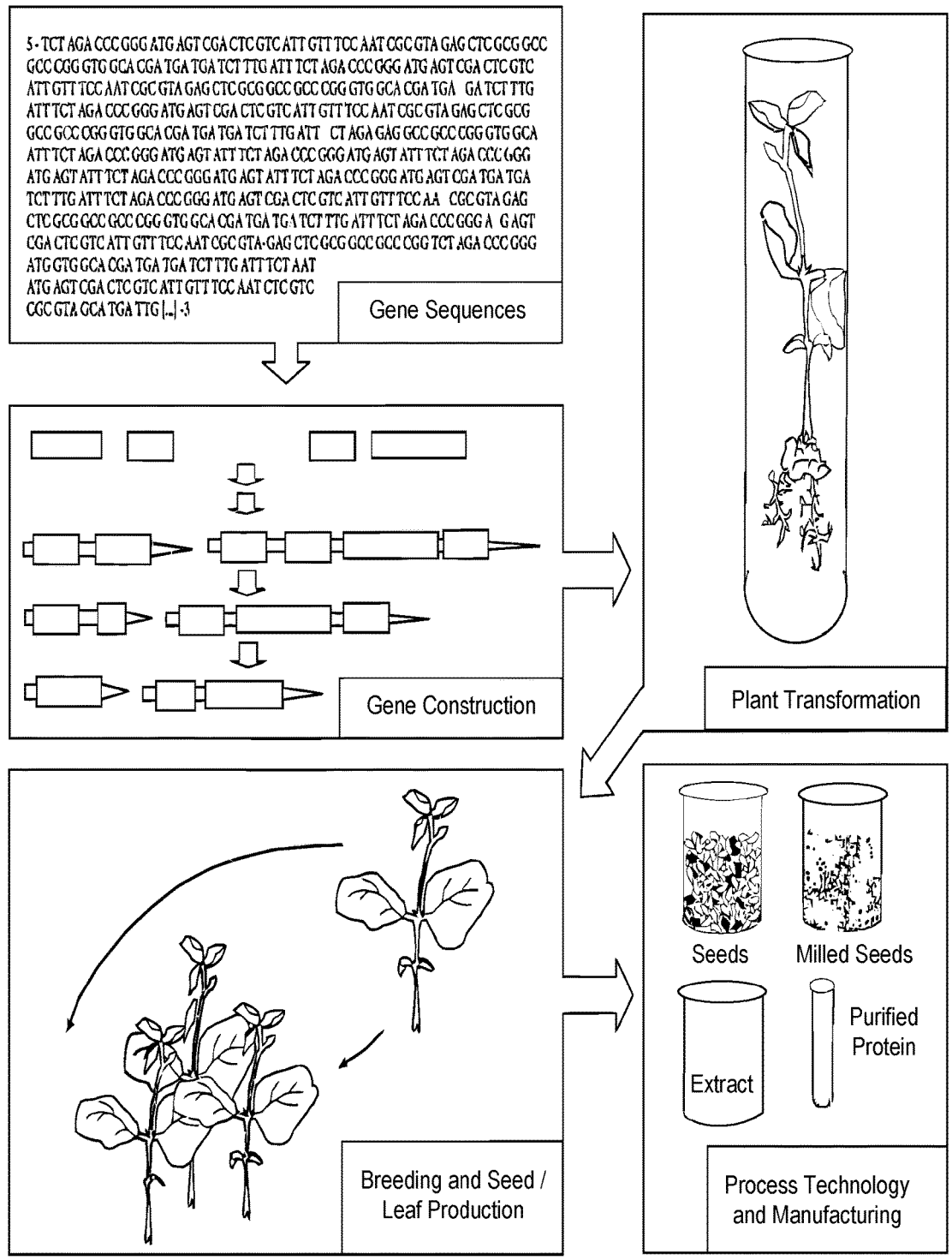
FIG. 18 illustrates an example of a process.

FIGS. 17 and 18 illustrate various techniques and technologies associated with plants. For example, consider Plant-Made Pharmaceuticals (PMPs), also referred to as pharming, which is a sub-sector of the biotechnology industry that involves the process of engineering plants (e.g., genetically, etc.) so that they can produce certain types of molecules such as peptides, secondary metabolites, etc. As an example, molecules may be harvested and used to produce pharmaceuticals or other products, optionally as adjuvants, additives, etc.

While plant cell cultures or hairy root systems are propagated in contained environments (vessels) the large-scale cultivation of transgenic plants is carried out in greenhouses or, for reasons of economy and scalability, in the field. A series of varying environmental factors must be taken into account at this step. They include light intensity, temperature, water regime, soil quality, the kind of fertilization, the presence of pests and the substances utilized to treat them. Such factors can impact the level of the quantity of the yield and the level of its quality.

As an example, ZMapp may be manufactured in the tobacco plant *Nicotiana benthamiana* in a bioproduction process. ZMapp is composed of three monoclonal antibodies (mAbs) that have been chimerized by genetic engineering.

An essential oil may be defined as a concentrated hydrophobic liquid containing volatile aroma compounds from plants. Essential oils may also be known as volatile oils, ethereal oils, aetherolea, or as the "oil of" a plant from which they were extracted, such as oil of clove. An oil is "essential" in the sense that it contains the "essence of" the plant's fragrance—the characteristic fragrance of the plant from which it is derived.

Some examples of plants and plant products include: Berries (Allspice, Juniper), Seeds (Almond, Anise, Buchu, Celery, Cumin, Nutmeg oil), Bark (Cassia, Cinnamon, Sassafras), Wood (Camphor, Cedar, Rosewood, Sandalwood, Agarwood), Rhizome (Galangal, Ginger), Leaves (Basil, Bay leaf, Buchu, Cinnamon, Common sage, Eucalyptus, Guava, Lemon grass, Melaleuca, Oregano, Patchouli, Peppermint, Pine, Rosemary, Spearmint, Tea tree, Thyme, Tsuga, Wintergreen), Resin (Benzoin, Copaiba, Frankincense, Myrrh), Flowers (Cannabis, Chamomile, Clary sage, Clove, Scented geranium, Hops, Hyssop, Jasmine, Lavender, Manuka, Marjoram, Orange, Rose, Ylang-ylang), Peel (Bergamot, Grapefruit, Lemon, Lime, Orange, Tangerine), Root (Valerian, etc.).

Figure 19:
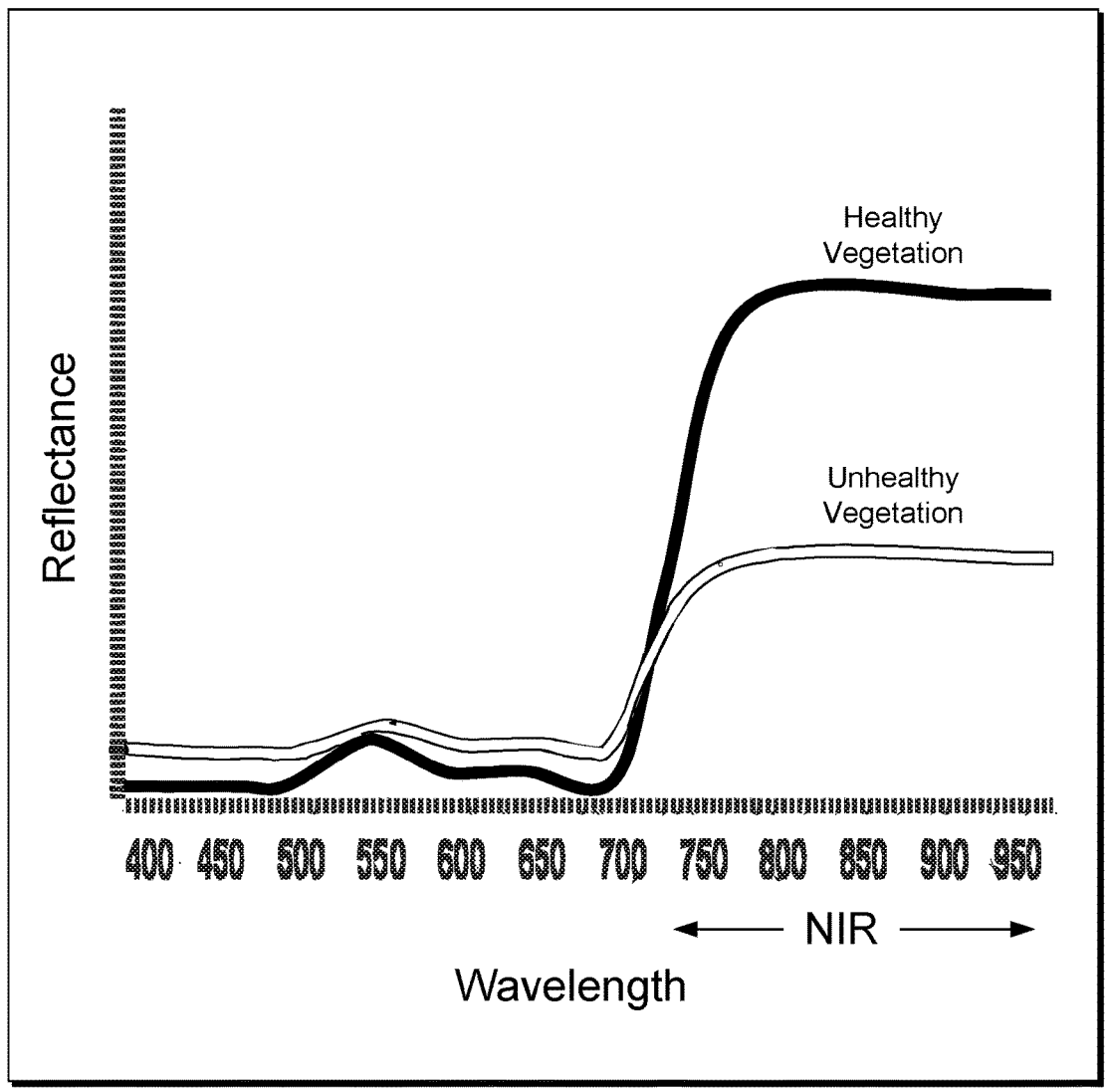
FIG. 19 illustrates an example of a method.

FIG. 19 shows an example of a technique that can monitor plant stress. As an example, a system may include one or more sensors (e.g., cameras, etc.) that can acquire information about a plant, a portion of a plant, plants, etc.

FIG. 20 shows an example of a system 2010 and an example of a method 2060. The system 2010 includes one or more sensors and one or more LEDs. The system 2010 may be applied to one or more plants. The method 2060 includes an LED on block 2062 for turning on an LED unit to illuminate one or more plants, a sense block 2064 for sensing information about at least one of the one or more plants, an analysis block 2066 for analyzing at least the sensed information, an adjustment block 2068 for adjusting at least one parameter associated with, for example, the illumination and a harvest block 2070 for harvesting one or more plants, one or more portions of a plant, etc.

As an example, hyperspectral imaging may be employed, for example, to estimate chlorophyll content and/or distribution of a vital compound(s) on a portion of a plant. Such a technique may provide information as to dynamics of stress on, for example, a leaf level. As an example, via characteristic reference spectra, a method may include identifying one or more stress factors. As an example, a system may include a controller that can control one or more emission related parameters such as, for example, duration, wavelength(s), intensity, etc.

As an example, a system may include one or more components of a Tetracam Multi-spectral Imaging System (Chatsworth, Calif.). Such systems include one or more cameras that are sensitive to visible and near-infra-red light. Such systems may aim to acquire information as to whether a plant is healthy or not (e.g., level of stress, etc.), for example, as healthy plants tend to reflect near-infrared light much better than unhealthy plants. As an example, a controller may receive information acquired at least in part via a multispectral imaging system and control one or more parameters associated with an emission system (e.g., LEDs, lasers, etc.).

As an example, a system may include one or more NIR sensors. As an example, information sensed via one or more NIR sensors may be analyzed as to a physiologic condition or conditions, whether mammalian or plant.

As an example, a system may include a sensor to sense temperature at a surface of a leaf or leaves. As an example, a correlation may exist between plants stress levels and a rise in leaf temperature, for example, a rise above ambient air temperature. As an example, a method may include recording one or more differential temperatures between ambient air and foliage temperatures where, for example, magnitude of such differential(s) may be a measure of stress level of one or more plants.

As an example, a system may include circuitry that can perform machine learning. As an example, such machine learning may be applied to one or more techniques for treatment of mammals and/or plants. As an example, a system may include circuitry that can implement one or more fuzzy logic algorithms (e.g., for control of emissions for treatment, etc.).

Figure 21:
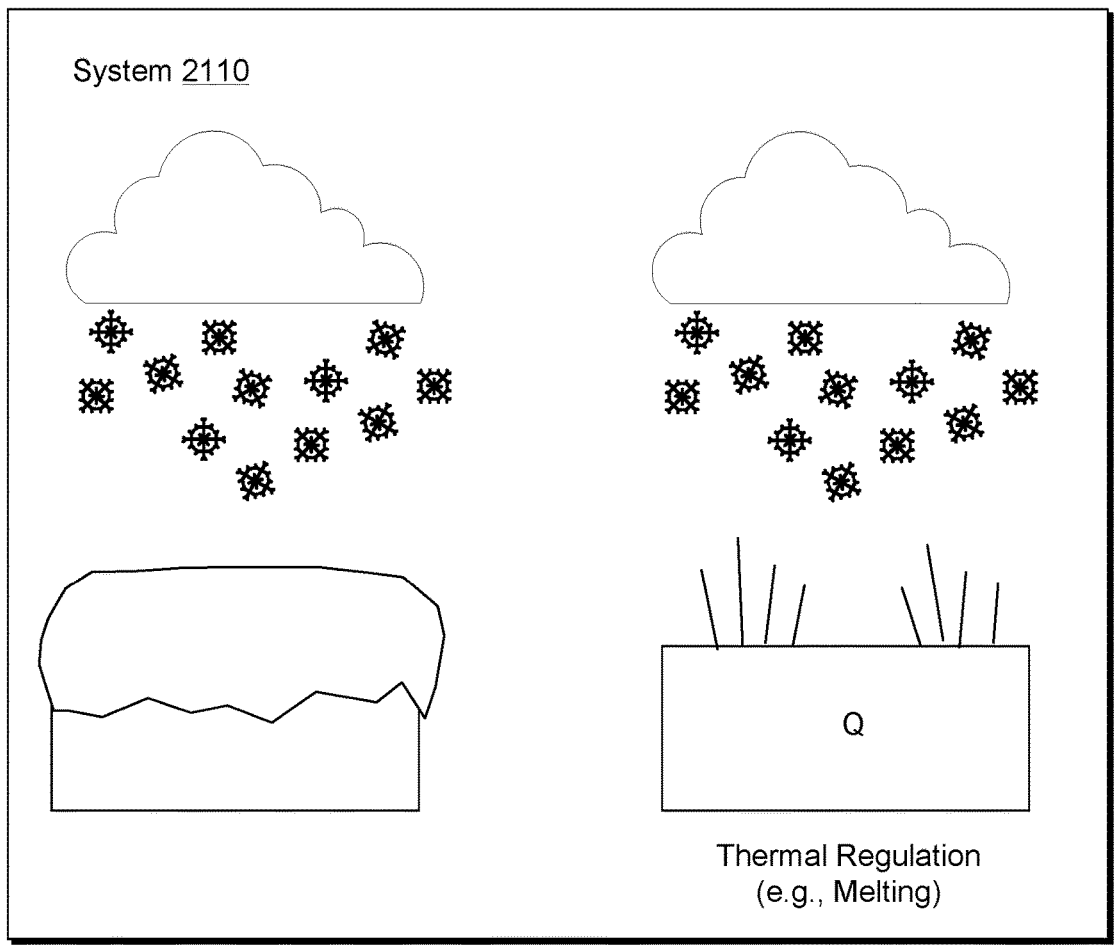
FIG. 21 illustrates an example of a system and an example of a method.

FIG. 21 shows an example of a system 2100 that can include controlling heat, for example, for one or more purposes. For example, in weather where moisture (e.g., ice, snow, etc.) may accumulate on a lens, LEDs, etc., the amount of heat generated by the LEDs may not be sufficient to prevent the moisture from accumulating. In such a scenario, a heater may be included in a system. As an example, a system may include heat transfer equipment (e.g., one or more heat transfer units). As an example, consider a fan or fans and/or a heater or heaters. As an example, a system may regulate a cooling unit such that heat energy can cause melting of existing snow, ice, etc. and/or to prevent accumulation of snow, ice, etc. For example, a cooling unit may be regulated to allow for more heat build-up. As another example, a cooling unit may move air or other fluid in one or more paths, which may optionally include a path that is directed toward a wall that includes a surface on which snow, ice, etc. may accumulate. As an example, a method may include increasing power supplied to one or more LEDs such that the one or more LEDs generate more heat energy, which, in turn, can cause existing snow, ice, etc. to melt and/or to prevent snow, ice, etc. from accumulating and blocking emissions of light from the one or more LEDs. As an example, in combination with current control and temperature metering, a system may provide more light and hence melt down the ice, optionally in a manner such that the system does not necessarily need a specialized heater or a supplemental heater (e.g., an external heating unit, etc.).

Figure 22:
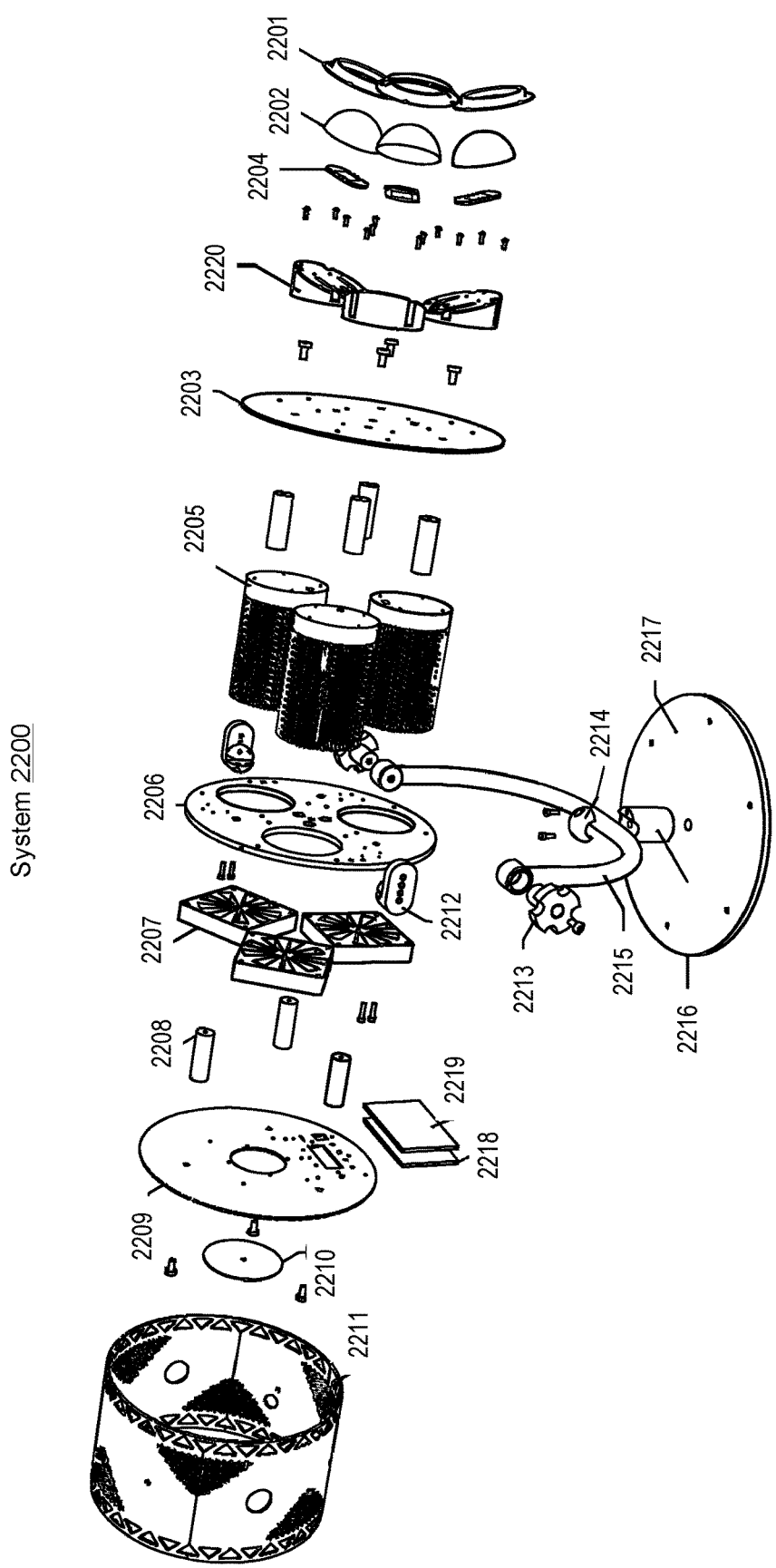
FIG. 22 illustrates an example of a system.

FIG. 22 shows an example of a system 2200, which may be an illumination device. As shown in FIG. 22, the system 2200 can include one or more of a lens retaining ring 2201, a glass optic lens 2202, a lens plate 2203, a LED module 2204, a heat sink 2205, a fan plate 2206, a fan 2207, a spacer 2208, a control plate 2209, an antenna cap 2210, a lamp skirt 2211, an armature mount 2212, a clamping know 2213, a stand adapter cap 2214, an armature weldment 2215, a stand adapter mount 2216, a stand base plate 2217, a U/I board 2218, an I/O board 2219 and an LED wedge 2220 (e.g., an LED assembly with a plurality of individual LEDs). In the example of FIG. 22, the system 2200 includes three LED assemblies 2220 and three corresponding fans 2207.

FIG. 23 shows a block diagram of an example of a controller 2300. In the example of FIG. 23, the controller 2300 can include an ARM processor such as, for example, an ARM Cortex processor. As an example, consider the ARM Cortex M-3 processor, which includes three AHB-Lite buses (e.g., system bus, I-code bus, and D-code bus). As an example, use of two core buses can allow for simultaneous operations (e.g., where concurrent operations can target different devices). As an example, the controller 2300 can be of a family of LPC17xx controllers as marketed by NXP Semiconductors NV (Eindhoven, Netherlands), which can be ARM processor-based microcontrollers. As an example, a multi-layer AHB matrix can connect ARM Cortex-M3 buses and other bus masters to peripherals where peripherals that are on different slave ports of the matrix can be accessed simultaneously by different bus masters.

As an example, a microprocessor (e.g., ARM, etc.) can be a general purpose, 32-bit microprocessor or 64-bit microprocessor that may be operable at relatively low power consumption. As an example, a controller can include on-chip flash program memory and, for example, a multi-port flash accelerator that can be used with AHB-Lite buses. As an example, a controller can include on-chip SRAM, for example, accessible by a microprocessor and, for example, a DMA controller and, for example, additional SRAM blocks situated on a separate slave port on the AHB multi-layer matrix. As an example, an architecture such as that of the controller 2300 may allow for accesses to be spread over multiple separate RAMS that can be accessed simultaneously. As an example, a memory protection unit (MPU) may be used to improve reliability of an embedded system by protecting certain data within a user application.

Figure 24:
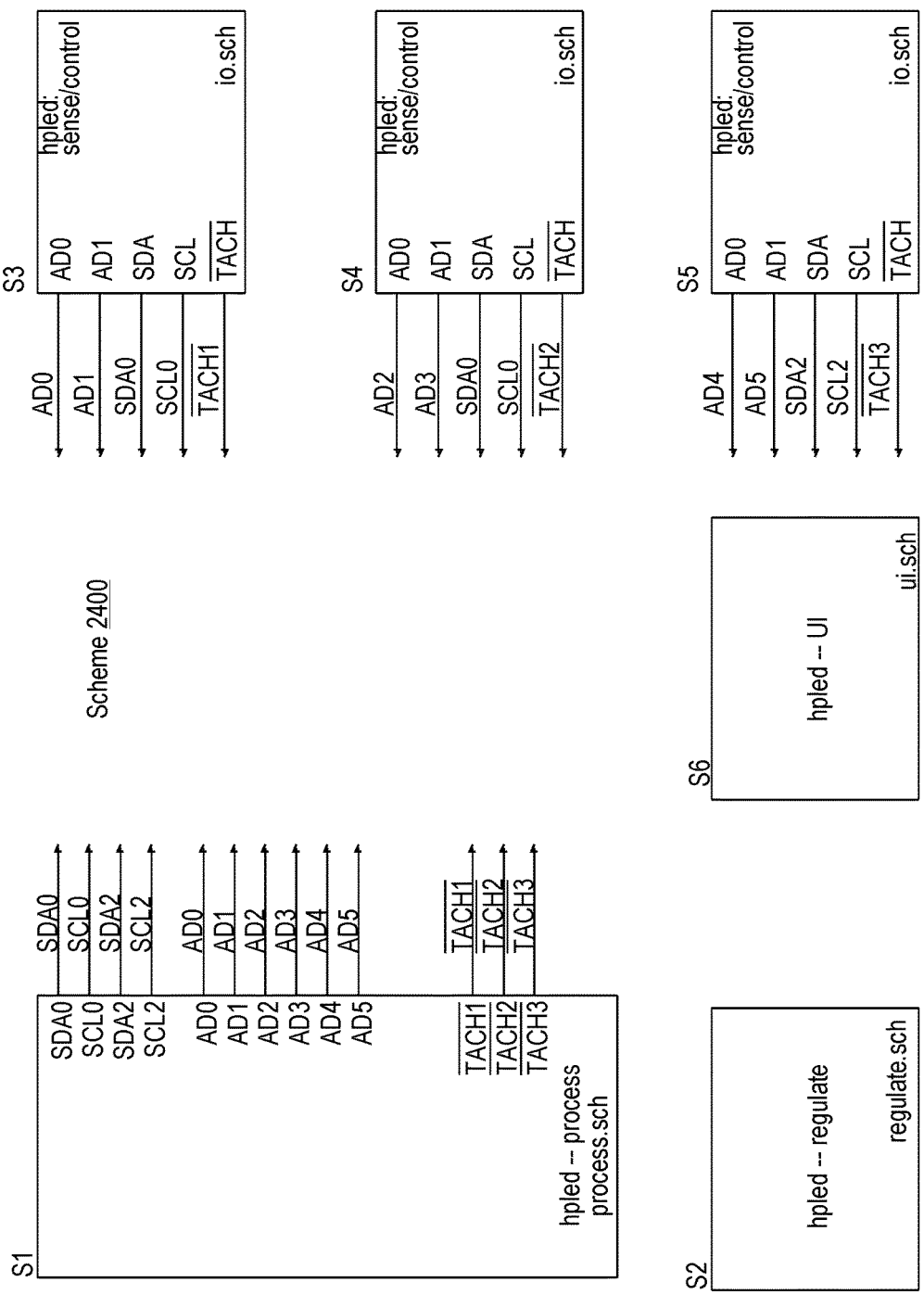
FIG. 24 illustrates an example of a scheme.

FIG. 24 shows an example of a scheme 2400, for example, with respect to various scheduler modules. As shown, the scheme can include scheduler modules process.sch (e.g., associated with various circuitry), regulate.sch (e.g., associated with regulation circuitry), ui.sch (e.g., associated with a user interface such as a touchscreen display, etc.) and a plurality of io.sch (e.g., associated with component I/Os).

Figure 25:
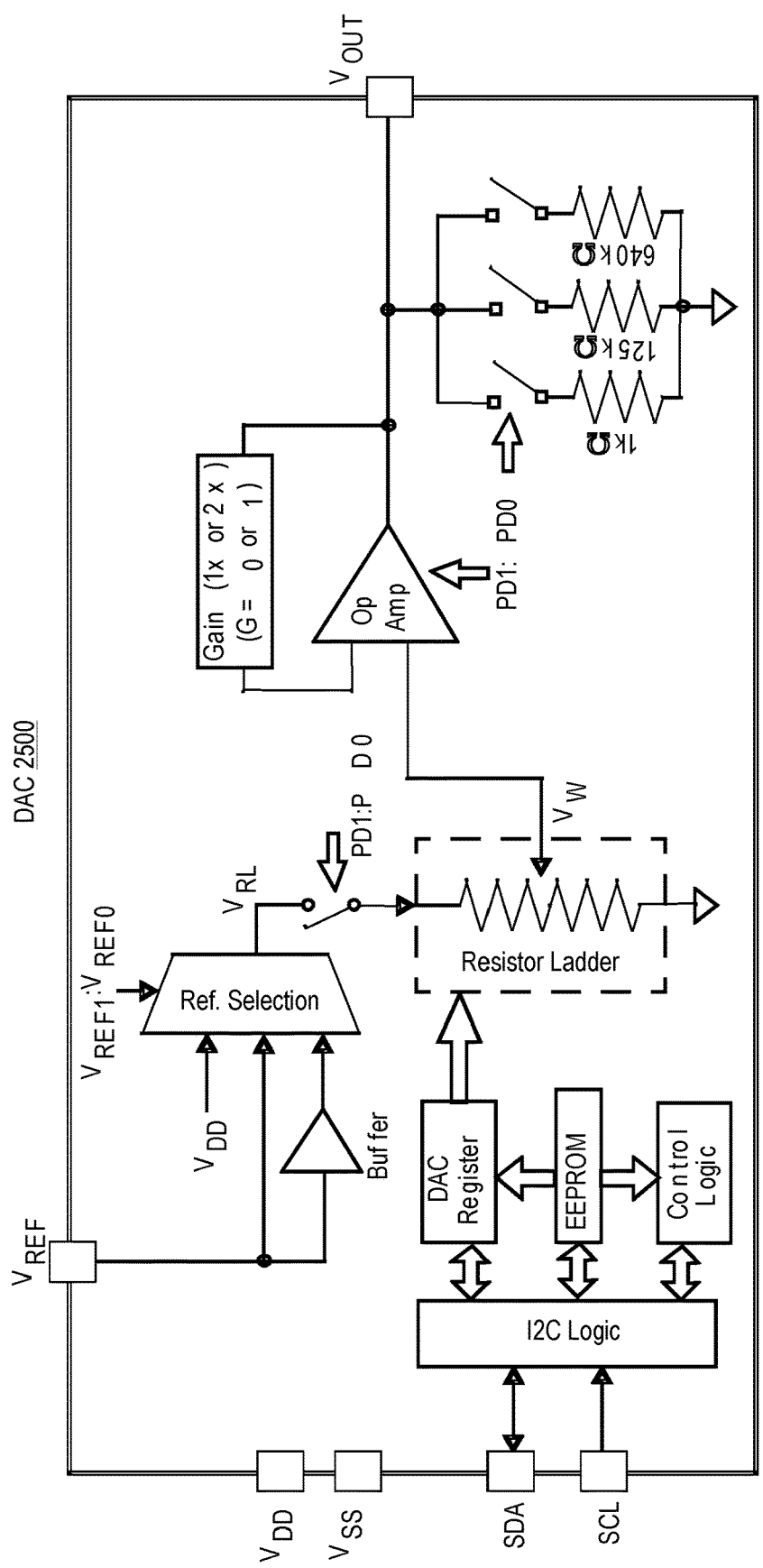
FIG. 25 illustrates an example of a digital to analog converter.

FIG. 25 shows an example of a digital to analog converter (DAC) 2500. In the example of FIG. 25, the DAC includes nonvolatile memory and an I²C serial interface. As shown, digital information provided at the interface can result in a voltage $V_{OUT}$. Such output may be operatively coupled electrically to an operational amplifier, for example, as illustrated in the example of FIG. 4 (e.g., where pin 1 is $V_{OUT}$). As an example, an interface may operate in one or more modes, for example, consider a standard mode (e.g., about 100 kHz or kbps), a fast mode (e.g., 400 kHz or kbps) and a high-speed mode (e.g., 3.4 MHz or Mbps). As an example, a controller can include a serial interface that can be operatively coupled to a serial interface of a DAC. As an example, a controller may be operatively coupled to a plurality of DACs. As an example, a DAC may be associated with an LED unit. As an example, a DAC may be associated with an air mover such as a fan. As an example, a LED unit can be associated with a fan where the LED unit and the fan are operated at least in part via digital input to respective DACs that convert digital information, for example, to voltages, which may be operatively coupled to circuitry such as respective operational amplifiers (see, e.g., FIG. 4). As an example, a controller may generate output via an I2C interface where such output can be received as input to a DAC, for example, via an I2C interface of the DAC.

As an example, a controller may control operation of a plurality of LED units and a plurality of fans where a correspondence can exist between LED units and fans (e.g., a one to one correspondence, etc.).

As an example, a system may regulate performance of a plurality of LEDs such that the LEDs emit relatively flicker-free radiation (e.g., light, etc.). For example, the emissions of the LEDs may be relatively free of low level frequency drifts. As an example, emissions of LEDs may be relatively free of drift in intensity, drift in wavelength, etc. As an example, a system can include regulating temperature such that temperature effects on LED performance are minimized. Such temperature regulation may account for heat generated by one or more components during operation, for example, at least in part by control of one or more air movers (e.g., one or more fans). As an example, regulation of LED assemblies that include multiple LEDs may be via a respective air mover or a respective set of air movers where regulation may be independent from that of one or more other LED assemblies of a system. As illustrated in the example system 2200 of FIG. 22, a one-to-one correspondence can exist between LED assemblies 2220 and fans 2207.

As an example, a system may be implemented for one or optionally more of the following types of treatment: Hair Growth, Infrared pain treatment, Wound healing, Photorejuvenation, Lipolysis, SAD—Seasonal Affective Disorder, Acne, Pre and/or post surgery (see, e.g., Trelles et al., J Cosmet Laser Ther. 2006 April; 8 (1):39-42. Red light-emitting diode (LED) therapy accelerates wound healing post-blepharoplasty and periocular laser ablative resurfacing, which is incorporated by reference herein), Pain Management, postinflammatory conditions, Hyperpigmentation Prevention, Before $CO_2$ Ablation, Photoprophylaxis or Photoprevention, Photopreparation (e.g., to enhance penetration and effectives of active compounds), Photo Dynamic Therapy (PDT), Actinic Keratosis, Basal Cell Carcinoma, Oily skin Bowens Disease, Sebaceous gland disorders, photo damage, etc.

As an example, a system may include circuitry that can control one or more of Fan Speed and Light Intensity. As an example, a system may include circuitry that can measure one or more of Fan Speed and Temperature, optionally at one or more locations (e.g., at emission head, within equipment, etc.). As an example, a system may include circuitry that can receive information such as, for example, patient temperature (e.g., via an IR camera or other device). As an example, a system may include circuitry that can implement machine learning, fuzzy logic, etc., for example, to provide an accurate dosage, a low noise level, to help ensure equipment longevity and optionally to provide "early" warning of one or more conditions (e.g., malfunction, calibration, end-of-life of a component, security challenge/hack, etc.).

As an example, a system can include at least one Heat Dissipation Module; at least one DC Power Supply; at least one LED Module; at least one Discrete Power Transistor Module; at least one Control Module; and at least one Structural Housing. As an example, a control module can include at least one Electronic Component capable of independent current control of each LED Module. As an example, a DC Power Supply may include at least one Battery. As an example, an LED Module can include one or more LEDs where, for multiple LEDs, at least one may differ in wavelength from one or more others. As an example, LEDs may optionally be controlled independently. As an example, groups of LEDs may optionally be controlled independently. As an example, a system may include a Firmware Component that may, for example, include at least one external Signal interface that can output a signal and at least one remote Intelligent Control Module that can based on the signal control an LED or LEDs (e.g., with one or more controllable parameters).

As an example, a system may include circuitry that acts to minimize equipment noise within maximum noise constraints imposed by a user while being able to achieve an optimal (e.g., best possible) light output within proper thermal management boundaries. As an example, a system may include circuitry that can request preventive maintenance of one or more components (e.g., fans and equipment based on equipment sensor data such as, for example, fan speed, LED temperature, etc.). As an example, a system may include circuitry that can modulate amplitude and/or frequency of emitted energy (e.g., light, etc.) with minimal noise.

As an example, a system may control fan speed to minimize noise and/or to maximize life of a fan or fans. As an example, a system may adjust power supplied to one or more LEDs and may optionally compensate with appropriate time exposure to ensure dosage delivery. As an example, a system may act to alert an operator as to preventive maintenance of one or more fans, which may be inferred from temperature and fan speed, for example, in an effort to minimize downtime. As an example, a system may include circuitry that can aim to deliver consistent results in different and changing environment temperature conditions (e.g., ambient condition changes such as, for example, humidity, temperature, etc.). As an example, a system may aim to limit ambient temperature increase that may be due in part to operation of the system. As an example, a system may include logging circuitry that can maintain a log or logs, which may optionally be encrypted, stored locally and/or remotely, etc.

As an example, an I/O module of a system may measure fan speed, temperature and over-current conditions. As an example, an I/O module may include circuitry for fan and power-led control signals (e.g., to a MOSFET board, etc.). As an example, a system may include one or more Discrete Power Transistor boards (e.g., operatively coupled to one or more LEDs, one or more fans, etc.).

As an example, a system may include a card reader that can read information from a storage medium (e.g., an SD card, etc.). As an example, a card reader may be configured to store information to a storage medium (e.g., an SD card, etc.). As an example, information may be encrypted and/or de-encrypted. As an example, a system may include a volatile storage medium and/or a non-volatile storage medium. As an example, a system may include circuitry that can provide for a publisher-subscriber event mechanism.

As an example, software and/or firmware executable via hardware may allow for user configurations to be stored on a medium such as, for example, an SD card. As an example, software and/or firmware may be executable via hardware to monitor one or more types of information such as, for example, fan speed, temperature, over-current indication, etc. As an example, software and/or firmware may be executable via hardware to set fan speed and LED current, for example, according to a configuration, using a PID fuzzy logic model.

As an example, a system may include a plurality of interfaces such as WIFI, ETHERNET, local display (e.g., local touchscreen), indicator lights, buttons, a rotary encoder, etc.

As an example, a system can include a LED unit socket; and LED supply circuitry that includes a digital to analog converter, an operational amplifier operatively coupled to an analog output of the digital to analog converter, and a metal-oxide-semiconductor field-effect transistor that includes a gate operatively coupled to an output of the operational amplifier, a source operatively coupled to an input of the operational amplifier and a drain operatively coupled to the LED unit socket. As an example, such a system can include fan circuitry.

As an example, a system can include a digital data bus operatively coupled to a digital input of a digital to analog converter. In such an example, the digital data bus can be, for example, a two wire bus. As an example, a digital data bus can be an I2C bus (e.g., I$^2$C bus).

As an example, a system can include a controller that includes a digital output operatively coupled to a digital input of a digital to analog converter.

As an example, a system can include an operational amplifier and a metal-oxide-semiconductor field-effect transistor that form a control loop. In such an example, the control loop can control amplification of analog signals output via the output of the operational amplifier.

As an example, a system can include a plurality of LED unit sockets. As an example, a system can include a plurality of LED unit sockets and a plurality of LED supply circuitries.

As an example, a system can include fan supply circuitry that includes a digital to analog converter. In such an example, the system can include a digital data bus operatively coupled to the digital to analog converter of the fan supply circuitry and operatively coupled to a digital to analog converter of LED supply circuitry. In such an example, the system can include a controller operatively coupled to the digital data bus where the controller includes control circuitry that controls the LED supply circuitry and that controls the fan supply circuitry.

As an example, a system can include a LED unit received by a LED unit socket. In such an example, the system can include a fan unit socket and a fan unit received by the fan unit socket. As an example, an LED unit can include a finned heat sink (e.g., with metal fins, alloy fins, composite material fins of heat conductive material, etc.).

As an example, a system can include a plurality of LED units received by respective LED unit sockets. As an example, a system can include an LED unit received by an LED unit socket where the LED unit can be of a power rating of approximately 100 W.

As an example, a system can include a power supply. In such an example, the power supply can include an output or outputs for an output voltage or output voltages in a range of approximately 30 volts to approximately 50 volts.

Although various examples of methods, devices, systems, designs, etc., have been described in language specific to structural features and/or methodological acts, it is to be understood that the subject matter defined in the appended claims is not necessarily limited to the specific features or acts described. Rather, the specific features and acts are disclosed as examples of forms of implementing the claimed methods, devices, systems, designs, etc.

What is claimed is:
1. A therapy system comprising:
a controller;

LEDs;
LED supply circuitry operatively coupled to the LEDs, wherein the controller is operatively coupled to the LED supply circuitry for control of the LED supply circuitry; and
a camera that comprises a near-infrared range and that senses information of an object, wherein the camera is operatively coupled to the controller and wherein the controller controls the LED supply circuitry to therapeutically illuminate the object via one or more of the LEDs using an illumination dosage service that regulates an illumination dosage delivered to the object, based at least in part on the information, by at least one of adjustment to power supplied to one or more of the LEDs and adjustment to illumination exposure time, to ensure delivery of the illumination dosage according to a therapeutic protocol.

2. The therapy system of claim 1 wherein the controller comprises thermal management circuitry that implements one or more thermal management services.

3. The therapy system of claim 2 wherein the thermal management services comprise the illumination dosage service.

4. The therapy system of claim 2 wherein the thermal management services comprise a temperature regulation service that regulates temperature of at least one of the LEDs.

5. The therapy system of claim 2 wherein the thermal management services comprise a temperature regulation service that regulates temperature of at least one of the LEDs and the illumination dosage service that regulates illumination dosage delivered to the object, wherein the temperature regulation service minimizes noise of illumination within maximum noise constraints to maintain a desired illumination wavelength or wavelengths for the delivery of the illumination dosage according to the therapeutic protocol.

6. The therapy system of claim 1 wherein the camera senses distance information of the object.

7. The therapy system of claim 1 wherein the camera senses temperature information of the object.

8. The therapy system of claim 1 wherein the camera senses skin information of skin of the object.

9. The therapy system of claim 8 wherein the information comprises skin color information.

10. The therapy system of claim 1 wherein the object is a mammalian object and wherein the controller analyzes the information as to a physiologic condition or conditions of the mammalian object.

11. The therapy system of claim 1 wherein the object is a plant object and wherein the controller analyzes the information as to a physiologic condition or conditions of the plant object.

12. The therapy system of claim 11 wherein the information comprises temperature of a surface of a leaf.

13. The therapy system of claim 12 wherein the controller operates based at least in part on a correlation between plant stress levels and a rise in the temperature of the leaf.

14. The therapy system of claim 1 comprising an LED unit that comprises at least a portion of the LEDs wherein the LED comprises a power rating of 100 W.

15. The therapy system of claim 1 further comprising a power supply.

16. The therapy system of claim 15 wherein the power supply comprises an output voltage in a range of approximately 30 volts to approximately 50 volts.

17. A method comprising:
in a therapy system that comprises a controller; LEDs; LED supply circuitry operatively coupled to the LEDs, wherein the controller is operatively coupled to the LED supply circuitry for control of the LED supply circuitry; and a camera that comprises a near-infrared range and that senses information of an object, wherein the camera is operatively coupled to the controller and wherein the controller controls the LED supply circuitry to therapeutically illuminate the object via one or more of the LEDs using an illumination dosage service that regulates an illumination dosage delivered to the object, based at least in part on the information, by at least one of adjustment to power supplied to one or more of the LEDs and adjustment to illumination exposure time, to ensure delivery of the illumination dosage according to a therapeutic protocol, sensing information of the object; and
controlling the LED supply circuitry based at least in part on the information to therapeutically illuminate the object via one or more of the LEDs to ensure delivery of the illumination dosage according to the therapeutic protocol.

18. The method of claim 17 comprising utilizing thermal management services that comprise a temperature regulation service for regulating temperature of at least one of the LEDs and the illumination dosage service for regulating the illumination dosage delivered to the object, wherein the temperature regulation service minimizes noise of illumination within maximum noise constraints to maintain a desired illumination wavelength or wavelengths for the delivery of the illumination dosage according to the therapeutic protocol.

* * * * *